United States Patent
Germain et al.

(10) Patent No.: US 12,280,520 B2
(45) Date of Patent: *Apr. 22, 2025

(54) ARTHROSCOPIC DEVICES AND METHODS

(71) Applicant: Relign Corporation, Campbell, CA (US)

(72) Inventors: Aaron Germain, San Jose, CA (US); Kyle Klein, San Jose, CA (US); Jan Echeverry, San Jose, CA (US)

(73) Assignee: Relign Corporation, Campbell, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/409,356

(22) Filed: Jan. 10, 2024

(65) Prior Publication Data

US 2024/0139997 A1 May 2, 2024

Related U.S. Application Data

(60) Continuation of application No. 16/926,566, filed on Jul. 10, 2020, now abandoned, which is a continuation of application No. 15/832,292, filed on Dec. 5, 2017, now Pat. No. 10,744,672, which is a division of application No. 15/271,184, filed on Sep. 20, 2016, now Pat. No. 9,855,675.

(51) Int. Cl.
| | | |
|---|---|---|
| *B28B 1/24* | (2006.01) | |
| *A61B 17/32* | (2006.01) | |
| *A61B 17/3207* | (2006.01) | |
| *B28B 7/28* | (2006.01) | |
| *B28B 7/30* | (2006.01) | |
| *B28B 11/24* | (2006.01) | |
| *A61B 17/00* | (2006.01) | |

(52) U.S. Cl.
CPC .......... *B28B 1/24* (2013.01); *A61B 17/32002* (2013.01); *A61B 17/3207* (2013.01); *B28B 7/28* (2013.01); *B28B 7/303* (2013.01); *B28B 11/243* (2013.01); *A61B 2017/00526* (2013.01); *A61B 2017/0088* (2013.01); *A61B 2217/005* (2013.01)

(58) Field of Classification Search
CPC . A61B 17/3207; A61B 17/32002; B28B 1/24; B28B 11/243; B28B 7/303; B28B 7/28
See application file for complete search history.

(56) References Cited

U.S. PATENT DOCUMENTS

| | | |
|---|---|---|
| 3,758,253 A | 9/1973 | Pearne |
| 4,445,509 A | 5/1984 | Auth |
| 4,709,757 A | 12/1987 | Bly |
| 4,873,043 A | 10/1989 | Meyers |
| 5,038,455 A | 8/1991 | Guest |
| 5,041,256 A | 8/1991 | Petty et al. |
| 5,104,606 A | 4/1992 | Donoghue |
| 5,135,700 A | 8/1992 | Williams et al. |
| 5,217,671 A | 6/1993 | Moriuchi et al. |
| 5,456,593 A | 10/1995 | Kleyn |
| 5,498,387 A | 3/1996 | Carter et al. |
| 5,533,247 A | 7/1996 | Ishii et al. |
| 5,540,582 A | 7/1996 | Catalanotti et al. |
| 5,595,702 A | 1/1997 | Hiroki et al. |
| 5,624,694 A | 4/1997 | Delaby et al. |
| 5,690,660 A | 11/1997 | Kauker et al. |
| 5,702,736 A | 12/1997 | Henein |
| 5,804,123 A | 9/1998 | Klomhaus et al. |
| 5,814,356 A | 9/1998 | Ito et al. |
| 5,857,995 A | 1/1999 | Thomas et al. |
| 6,053,928 A | 4/2000 | Van Wyk et al. |
| 6,096,257 A | 8/2000 | Okabe et al. |
| 6,116,891 A | 9/2000 | Starkey |
| 6,656,195 B2 | 12/2003 | Peters et al. |
| 7,074,224 B2 | 7/2006 | Daniels et al. |
| 7,717,710 B2 | 5/2010 | Danger et al. |
| 8,663,227 B2 | 3/2014 | To |
| 9,585,675 B1 | 3/2017 | Germain et al. |
| 9,681,881 B1 | 6/2017 | Billiet et al. |
| 9,855,675 B1 | 1/2018 | Germain et al. |
| 10,028,767 B2 | 7/2018 | Germain et al. |
| 10,279,439 B1 | 5/2019 | Tinholt |
| 10,335,170 B2 | 7/2019 | Victor et al. |

(Continued)

FOREIGN PATENT DOCUMENTS

| | | |
|---|---|---|
| CN | 1791484 A | 6/2006 |
| CN | 102438789 A | 5/2012 |

(Continued)

OTHER PUBLICATIONS

"U.S. Appl. No. 15/271,184, Non Final Office Action mailed Aug. 30, 2017", 8 pgs.
"U.S. Appl. No. 15/271,184, Notice of Allowance mailed Nov. 3, 2017", 9 pgs.
"U.S. Appl. No. 15/271,184, Response filed Jun. 9, 2017 to Restriction Requirement mailed Apr. 27, 2017", 1 pg.
"U.S. Appl. No. 15/271,184, Response filed Oct. 9, 2017 to Non Final Office Action mailed Aug. 30, 2017", 5 pgs.
"U.S. Appl. No. 15/271,184, Restriction Requirement mailed Apr. 27, 2017", 11 pgs.
"U.S. Appl. No. 15/832,292, Non Final Office Action mailed Jan. 2, 2020", 16 pgs.

(Continued)

*Primary Examiner* — Emmanuel S Luk
(74) *Attorney, Agent, or Firm* — SCHWEGMAN LUNDBERG & WOESSNER, P.A.

(57) ABSTRACT

An arthroscopic or other surgical cutter has features which facilitate fabrication by ceramic molding. The arthroscopic cutter includes a cutter body having a longitudinal axis and a window, an interior channel, and a plurality of cutting edges extending radially outwardly from an outer surface thereof. The features include non-helical, longitudinally aligned cutting edges, controlled thicknesses of the cutting edges, controlled heights of the cutting edges, controlled areas of the windows, controlled diameters of the internal channels, controlled rake angles of the cutting edges, and other parameters.

20 Claims, 23 Drawing Sheets

(56) References Cited

U.S. PATENT DOCUMENTS

| | | |
|---|---|---|
| 10,415,319 B2 | 9/2019 | Olsen |
| 10,744,672 B2 | 8/2020 | Germain et al. |
| 10,849,648 B2 | 12/2020 | Germain et al. |
| 11,504,152 B2 | 11/2022 | Malkevich et al. |
| 11,576,699 B2 | 2/2023 | Germain et al. |
| 2002/0038129 A1 | 3/2002 | Peters et al. |
| 2002/0074694 A1 | 6/2002 | Kurimoto |
| 2002/0142056 A1 | 10/2002 | Aperce et al. |
| 2003/0015816 A1 | 1/2003 | Rapacki et al. |
| 2004/0137104 A1 | 7/2004 | Lu |
| 2004/0207108 A1 | 10/2004 | Pacchiana et al. |
| 2004/0265080 A1 | 12/2004 | Danielsson et al. |
| 2004/0267266 A1 | 12/2004 | Daniels et al. |
| 2005/0025594 A1 | 2/2005 | Lindblom |
| 2006/0127847 A1 | 6/2006 | Danger |
| 2008/0064303 A1 | 3/2008 | Gasser |
| 2008/0208249 A1 | 8/2008 | Blain et al. |
| 2010/0278604 A1 | 11/2010 | Glass et al. |
| 2012/0056351 A1 | 3/2012 | Xu |
| 2013/0017028 A1 | 1/2013 | Fang et al. |
| 2013/0121777 A1 | 5/2013 | Gey et al. |
| 2013/0223943 A1 | 8/2013 | Gey et al. |
| 2013/0240354 A1 | 9/2013 | Kajiyama et al. |
| 2013/0313403 A1 | 11/2013 | Atkins et al. |
| 2014/0374171 A1 | 12/2014 | Thomas |
| 2017/0066056 A1 | 3/2017 | Ronnheden et al. |
| 2017/0231643 A1 | 8/2017 | Victor et al. |
| 2018/0078279 A1 | 3/2018 | Germain et al. |
| 2018/0093391 A1 | 4/2018 | Germain et al. |
| 2018/0317957 A1 | 11/2018 | Germain et al. |
| 2019/0374246 A1 | 12/2019 | Malkevich et al. |
| 2021/0121198 A1 | 4/2021 | Germain et al. |
| 2021/0122082 A1 | 4/2021 | Germain et al. |

FOREIGN PATENT DOCUMENTS

| | | |
|---|---|---|
| CN | 102649180 A | 8/2012 |
| CN | 104551110 A | 4/2015 |
| CN | 110325129 A | 10/2019 |
| DE | 102012200045 A1 | 7/2013 |
| EP | 3515337 A1 | 7/2019 |
| JP | 2007503322 A | 2/2007 |
| JP | 2012524667 A | 10/2012 |
| JP | 2019529040 A | 10/2019 |
| KR | 101028889 B1 | 4/2011 |
| WO | WO-2018057527 A1 | 3/2018 |

OTHER PUBLICATIONS

"U.S. Appl. No. 15/832,292, Notice of Allowance mailed Apr. 14, 2020", 9 pgs.

"U.S. Appl. No. 15/832,292, Response filed Mar. 30, 2020 to Non Final Office Action mailed Jan. 2, 2020", 5 pgs.

"U.S. Appl. No. 16/926,566, Non Final Office Action mailed Aug. 23, 2023", 14 pgs.

"U.S. Appl. No. 16/926,566, Notice of Non-Compliant Amendment mailed Dec. 22, 2023", 5 pgs.

"U.S. Appl. No. 16/926,566, Preliminary Amendment Filed Apr. 7, 2021", 5 pgs.

"U.S. Appl. No. 16/926,566, Response filed Nov. 14, 2023 to Non Final Office Action mailed Aug. 23, 2023", 8 pgs.

"Chinese Application Serial No. 201780071602.8, Notification to Make Rectification mailed Jun. 6, 2019", with English translation, 2 pages.

"Chinese Application Serial No. 201780071602.8, Office Action mailed Nov. 19, 2021", W/English Translation, 20 pgs.

"Chinese Application Serial No. 201780071602.8, Response Filed Mar. 15, 2022 to Office Action mailed Nov. 19, 2021", w/English Claims, 22 pgs.

"Chinese Application Serial No. 201780071602.8, Response Filed Jul. 7, 2022 to Telephone Examiner Interview filed Jul. 4, 2022", w/ English claims, 15 pgs.

"European Application Serial No. 17853757.7, Extended European Search Report mailed May 4, 2020", 7 pgs.

"European Application Serial No. 17853757.7, Response filed Dec. 2, 2020 to Extended European Search Report mailed May 4, 2020", 59 pgs.

"International Application Serial No. PCT/US2017/052306, International Preliminary Report on Patentability mailed Apr. 4, 2019", 7 pgs.

"International Application Serial No. PCT/US2017/052306, International Search Report mailed Nov. 30, 2017", 2 pgs.

"International Application Serial No. PCT/US2017/052306, Written Opinion mailed Nov. 30, 2017", 7 pgs.

"Japanese Application Serial No. 2019-537027, Notification of Reasons for Refusal mailed Jul. 6, 2021", w/ English translation, 12 pgs.

"Japanese Application Serial No. 2019-537027, Office Action mailed Jul. 6, 2021", 25 pgs.

"Japanese Application Serial No. 2019-537027, Response filed Oct. 1, 2021 to Office Action mailed Jul. 6, 2021", w/ English claims, 13 pgs.

Pedowitz, et al., "Arthroscopic surgical tools: a source of metal particles and possible joint damage", Arthroscopy. 29(9), (2013), 1559-65.

Volpato, et al., "Application of Zirconia in Dentistry: Biological, Mechanical and Optical Considerations.", Advances in ceramics-electric and magnetic ceramics, bioceramics, ceramics and environment, (Sep. 2011), 397-420.

ARTHROSCOPIC DEVICES AND METHODS

CROSS-REFERENCE TO RELATED APPLICATION

This application is a continuation of U.S. patent application Ser. No. 15/832,292, filed Dec. 5, 2017, which is a divisional of U.S. patent application Ser. No. 15/271,184, filed Sep. 20, 2016, now U.S. Pat. No. 9,855,675, the entire content of which is incorporated herein by reference.

The disclosure of this application is related to that of application Ser. No. 15/271,187, filed on Sep. 20, 2016.

BACKGROUND OF THE APPLICATION

1. Field of the Invention

This invention relates to arthroscopic tissue cutting and removal devices by which anatomical tissues may be cut and removed from a joint or other site. More specifically, this invention relates to ceramic cutting members configured for use in arthroscopic cutters or shavers.

2. Description of the Background Art

In several surgical procedures including subacromial decompression, anterior cruciate ligament reconstruction involving notchplasty and arthroscopic resection of the acromioclavicular joint, there is a need for cutting and removal of bone and soft tissue. Currently, surgeons use arthroscopic shavers and burrs having rotational cutting surfaces to remove tissue for such procedures. A typical arthroscopic shaver or burr comprises a metal cutting member carried at the distal end of a metal sleeve that rotates within an open-ended metal shaft. A suction pathway for removal of bone fragments or other tissues is provided through a window proximal to the metal cutting member that communicates with a lumen in the sleeve.

When metal shavers and burrs 'wear' during a procedure, which occurs very rapidly when cutting bone, the wear can be characterized by loss of micro-particles from fracture and particle release which occurs along with dulling due to metal deformation. In such surgical applications, even very small amounts of such foreign particles that are not recovered from a treatment site can lead to detrimental effects on the patient health, with inflammation being typical. In some cases, the foreign particles can result in joint failure due to osteolysis, a term used to define inflammation due to presence of such foreign particles. A recent article describing such foreign particle induced inflammation is Pedowitz, et al. (2013) Arthroscopic surgical tools: "A source of metal particles and possible joint damage", Arthroscopy—The Journal of Arthroscopic and Related Surgery, 29(9), 1559-1565. In addition to causing inflammation, the presence of metal particles in a joint or other treatment site can cause serious problems for future MRIs. Typically, the MRI images will be blurred by agitation of the metal particles caused by the magnetic field used in the imaging, making assessments of the treatment difficult.

Another problem with the currently available metal shavers/burrs relates to manufacturing limitations in combination with the rapid dulling of metal cutting edges. Typically, a metal cutter is manufactured by machining the cutting surfaces and flutes into a burr or abrader surface. The flute shape and geometry can be limited since it is dictated by the machining process, and burr size and shape limitations may direct usage toward more coarse bone removal applications. Further, when operated in a rotational or oscillatory mode, the such cutting edges adapted for coarse bone removal may have a kickback effect as the flutes first make contact with bone, which is aggravated by rapid dulling of the machined cutting edges.

Therefore, the need exists for arthroscopic burrs and/or shavers that can operate to cut and remove bone without the release of fractured particles and micro-particles into the treatment site. Further, there is a need for burrs/cutters that do not wear rapidly and that can have cutting edges not limited by metal machining techniques. Additionally, there is a need for efficient methods and apparatus for manufacturing such improved arthroscopic burrs and/or shavers. At least some of these needs will be met by the inventions described below.

BRIEF SUMMARY OF THE INVENTION

The present invention provides a high-speed rotating cutter or cutting member that is fabricated entirely of a ceramic material. In one variation, the ceramic is a molded monolith with sharp cutting edges and is adapted to be motor driven at speeds of at least 1,000 rpm, typically ranging from 15,000 RPM to 20,000 RPM. The ceramic cutting member is coupled to an elongate inner sleeve that is configured to rotate within a metal, ceramic or composite outer sleeve. The ceramic material of the cutting member is exceptionally hard and durable and will not fracture and thus not leave foreign particles in a treatment site. In one aspect, the ceramic has a hardness of at least 8 Gpa (kg/mm$^2$) and a fracture toughness of at least 2 MPam$^{1/2}$. The "hardness" value is measured on a Vickers scale and "fracture toughness" is measured in MPam$^{1/2}$. Fracture toughness refers to a property which describes the ability of a material containing a flaw to resist further fracture and expresses a material's resistance to such fracture. In another aspect, it has been found that materials suitable for the cutting member of the invention have a certain hardness-to-fracture toughness ratio, which is a ratio of at least 0.5 to 1.

While the cutting assembly and ceramic cutting member of the invention have been designed for arthroscopic procedures, such devices can be fabricated in various cross-sections and lengths and can be use in other procedures for cutting bone, cartilage or soft tissue.

In particular, the present invention provides methods and apparatus for molding improved arthroscopic and other cutters and burrs, typically by molding ceramic materials.

In a first aspect, the present invention provides a method of fabricating a ceramic surgical cutting member of a type including a ceramic body having an outer surface, a longitudinal axis, a distal cutting portion with cutting edges, and a proximal shaft portion with a window that opens to an interior channel. The method comprises providing an injection mold with a mold cavity configured to form the outer surface of the cutting member, a first core pin which is configured to form the window of the cutting member, and a second core pin which is configured to form the interior channel. A flowable ceramic material is injected into the mold cavity to form the outer surface of the ceramic body. The first core pin is then removed from the mold to leave a void in the ceramic body which forms the window in the ceramic cutter body. The second core pin is removed from the mold to leave a void in the ceramic body which forms the interior channel of the ceramic cutter body. The at least first and second components of the mold components are then separated to allow release of the cutting member body from the mold cavity.

In particular embodiments of the methods, the cutting member body may be sintered after it has been released from the mold cavity to provide a hardened ceramic cutting member. Such sintered cutting members will typically have a hardness of at least 8 Gpa (kg/mm$^2$) and a fracture toughness of at least 2 MPam$^{1/2}$.

In other particular embodiments of the methods, the first core pin may be removed in a direction orthogonal to said longitudinal axis to form the window or the first core pin may be removed in a direction angled to said longitudinal axis to form the window. The second core pin may be removed in a direction aligned with said longitudinal axis to form the interior channel, and the at least first and second mold components may be separated in a direction orthogonal to the longitudinal axis of the ceramic cutter body. Alternatively, the at least first and second mold components may be separated in a direction aligned with the longitudinal axis of the ceramic cutter body. In still further embodiments of the methods of the preset invention, an additional mold component which forms helical cutting threads on the ceramic cutter body may be used and be separated by helical rotation of said mold component relative to the ceramic cutter body.

The mold cavity and mold components may be dimensioned and configured to provide cutter bodies which are particularly suitable for arthroscopic cutting. For example, the mold cavities may be configured and dimensioned to form a proximal shaft portion having a diameter ranging between 0.150 inch and 0.50 inch, to form a distal cutting portion having an outer diameter ranging between 0.170 inch and 0.60 inch., to form non-helical cutting edges, to form cutting edges aligned with the longitudinal axis, to form cutting edges with a radial rake angle ranging between 0° and 5°, to form cutting edges having a length ranging 0.10 inch to 0.40 inch, to form a window with an area ranging from 0.01 in$^2$ to 0.10 in$^2$, to form an interior channel with a mean cross-sectional width ranging from 0.008 inch to 0.40 inch, to form a window with edges having a sharp apex, to form a window with edges having a positive radial rake angle, and/or to form a window with edges having a radial rake angle greater than 15°.

In a second aspect, the present invention provides a mold assembly for fabricating a ceramic surgical cutting member of the type including a ceramic body having an outer surface, a longitudinal axis, a distal cutting portion with cutting edges, and a proximal shaft portion with a window that opens to an interior channel. The mold assembly comprises a main body mold component having (1) an internal mold cavity configured to receive a flowable material comprising a ceramic to form the outer surface of the cutting member, (2) a window aperture, and (3) an interior passage aperture. A first core pin is configured to pass through the widow aperture in the mold component to form the window of the cutting member, and a second core pin which is configured to pass through the interior channel aperture in the mold to form the interior channel of the cutting member. The interior channel aperture is oriented to align the second core pin axially through the mold component, and the window aperture is oriented to align the first core pin laterally through the mold component so that a distal end of the first core pin engages a side of the second core pin to connect the window of the cutting member to the interior passage of the cutting member so that tissue may be drawn through the window into the interior passage of a cutting member formed by the mold assembly.

In other particular embodiments of the mold assemblies, the main body mold component may include at least first and second subcomponents which are separable to allow release of the cutting member body from the main body mold component cavity. The mold assembly may further comprise an end cap component having an end mold cavity which aligns with the interior passage of the main body mold component to form the distal cutting portion with cutting edges of the cutting member. The first core pin may be oriented in an orthogonal direction relative to said longitudinal axis to form the window. Alternatively, the first core pin may be oriented in an angled direction relative to said longitudinal axis to form the window. The second core pin may be oriented in a direction aligned with said longitudinal axis to form the interior channel, and the at least first and second subcomponents may be configured to separate in a direction orthogonal to the longitudinal axis of the ceramic cutter body. The end cap may be configured to separate in a direction aligned with the longitudinal axis of the ceramic cutter body, and the end cap component may form helical cutting threads on the ceramic cutter body and be configured to separate from the mold assembly by helical rotation of said end cap relative to the ceramic cutter body. Alternatively, the end cap may be configured to form non-helical cutting edges on the ceramic cutter body.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION

The present invention relates to bone and cutting and removal devices and related methods of use. Variations of a ceramic cutter of the invention will be described to provide an overall understanding of the principles of the form, function and methods of use of the devices disclosed herein. In general, the present disclosure provides for an arthroscopic cutter for cutting bone that is disposable and is configured for detachable coupling to a non-disposable handle and motor drive component. This description of the general principles of this invention are not meant to limit the inventive concepts in the appended claims.

In general, the present invention provides a high-speed rotating ceramic cutter or burr that is configured for use in many arthroscopic surgical applications, including but not limited to treating bone in shoulders, knees, hips, wrists, ankles and the spine. More in particular, the device includes a cutting member that is fabricated entirely of a ceramic material that is extremely hard and durable, as described in detail below. A motor drive is operatively coupled to the ceramic cutter to rotate the burr edges at speeds of at least 1,000 rpm, typically ranging from 3,000 RPM to 20,000 RPM. As will be described further below, in a variation, the ceramic cutter is operated at 16,500 RPM for cutting bone.

Figure 1:
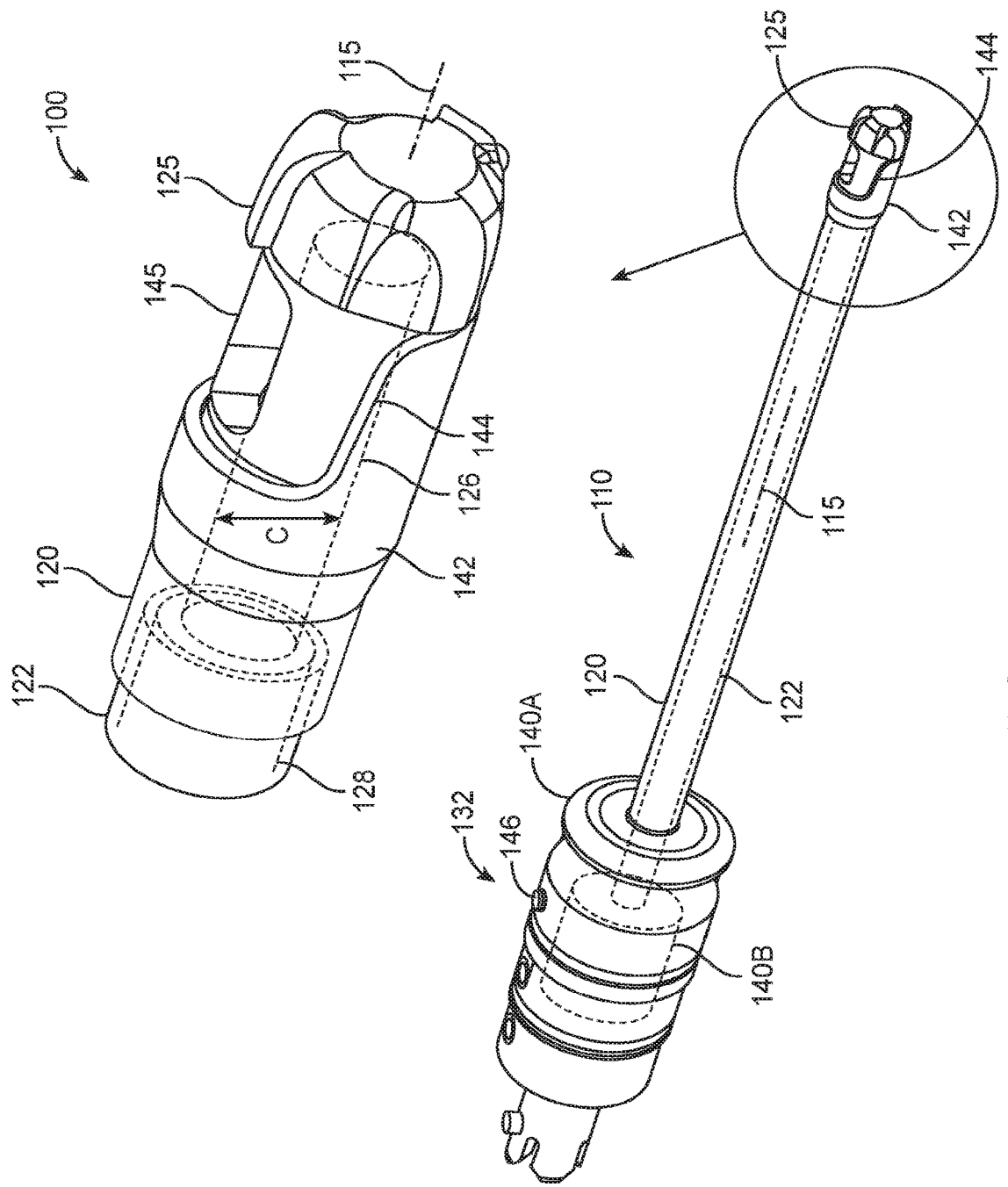
FIG. 1 is a perspective view of a disposable arthroscopic cutter or shaver assembly with a ceramic cutting member carried at the distal end of a rotatable inner sleeve with a window in the ceramic cutting member proximal to the distal cutting edges.
Figure 2:
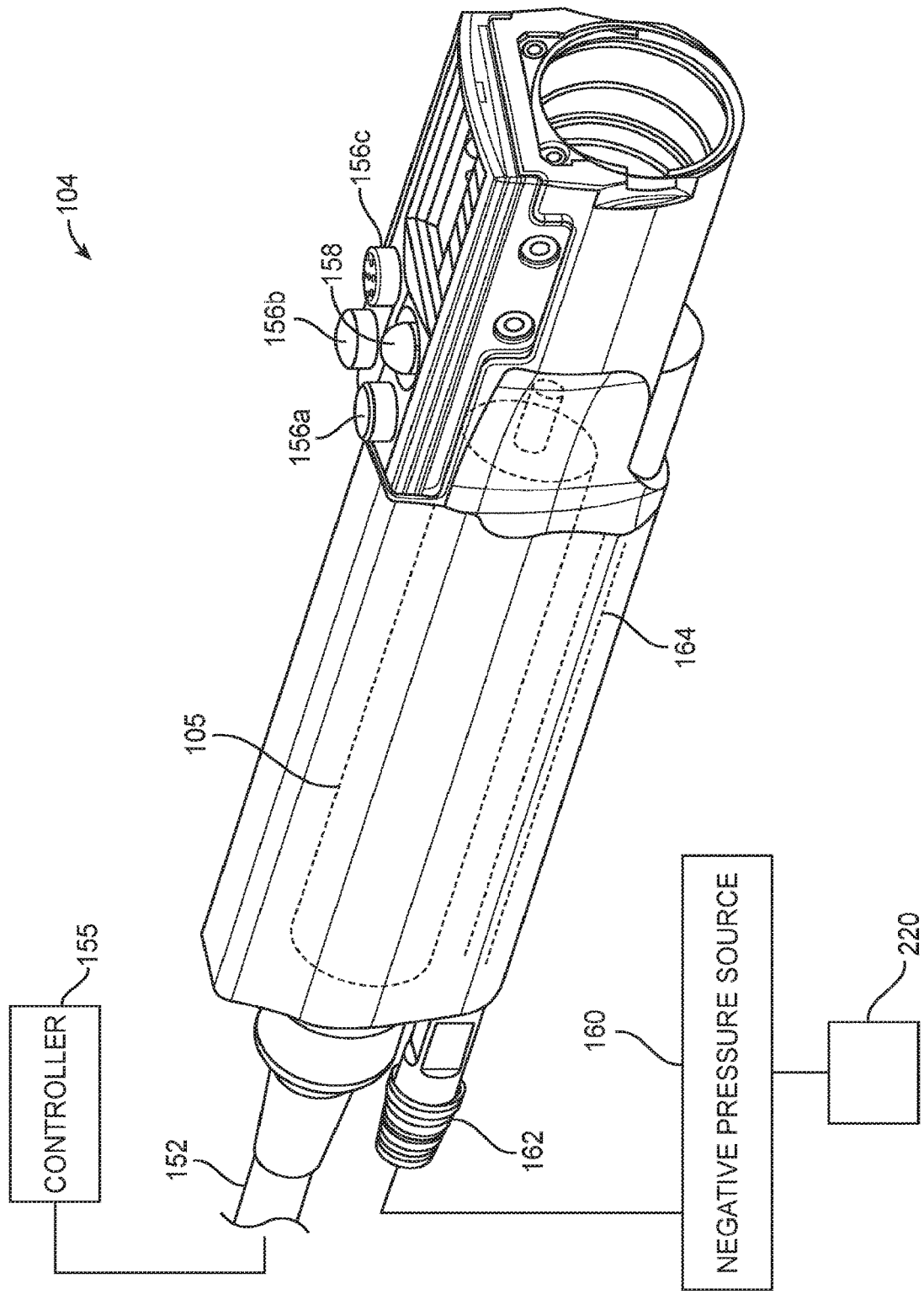
FIG. 2 is a perspective view of a handle body with a motor drive unit to which the cutter of FIG. 1 can be coupled, with the handle body including an LCD screen for displaying operating parameters of device during use together with a joystick and mode control actuators on the handle.

In one variation shown in FIGS. 1-2, an arthroscopic cutter or cutter assembly 100 is provided for cutting and removing hard tissue, which operates in an manner similar to commercially available metals shavers and burrs. FIG. 1 shows disposable cutter assembly 100 that is adapted for detachable coupling to a handle 104 and motor drive unit 105 therein as shown in FIG. 2.

The cutter assembly 100 of FIG. 1 has a shaft 110 extending along longitudinal axis 115 that comprises an outer sleeve 120 and an inner sleeve 122 rotatably disposed therein with the inner sleeve 122 carrying a distal ceramic cutting member 125 having an interior channel 126 therein that communicates with lumen 128 in the inner sleeve 122. The shaft 110 extends from a proximal hub assembly 132 wherein the outer sleeve 120 is coupled in a fixed manner to an outer hub 140A which can be an injection molded plastic, for example, with the outer sleeve 120 insert molded therein. The inner sleeve 122 is coupled to an inner hub 140B (phantom view) that is configured for coupling to the motor drive unit 105 (FIG. 2). The outer and inner sleeves 120 ands 122 typically can be a thin wall stainless steel tube, but other materials can be used such as ceramics, metals, plastics or combinations thereof.

Referring to FIG. 1, the outer sleeve 120 extends to distal sleeve region 142 that has an open end and cut-out 144 that is adapted to expose a window 145 in the ceramic cutting member 125 during a portion of the inner sleeve's rotation. The window 145 communicates with interior channel 126 in the cutting member 125. Referring to FIGS. 1 and 2, the proximal hub 132 of the cutter assembly 100 is configured with a J-lock, snap-fit feature, screw thread or other suitable feature for detachably locking the hub assembly 132 into the handle 104. As can be seen in FIG. 1, the outer hub 140A includes a projecting key 146 that is adapted to mate with a receiving J-lock slot in the handle 104 (see FIG. 2).

In FIG. 2, it can be seen that the handle 104 is operatively coupled by electrical cable 152 to a controller 155 which controls the motor drive unit 105. Actuator buttons 156a, 156b or 156c on the handle 104 can be used to select operating modes, such as various rotational modes for the ceramic cutting member. In one variation, a joystick 158 be moved forward and backward to adjust the rotational speed of the ceramic cutting member 125. The rotational speed of the cutter can continuously adjustable, or can be adjusted in increments up to 20,000 RPM. FIG. 2 further shows that negative pressure source 160 is coupled to aspiration connector 162 which communicates with a flow channel 164 in the handle 104 and through the shaver hub 132 (FIG. 1) to the lumen 128 in inner sleeve 122 which extends to window 145 in the ceramic cutting member 125 (FIG. 2).

Figure 3:
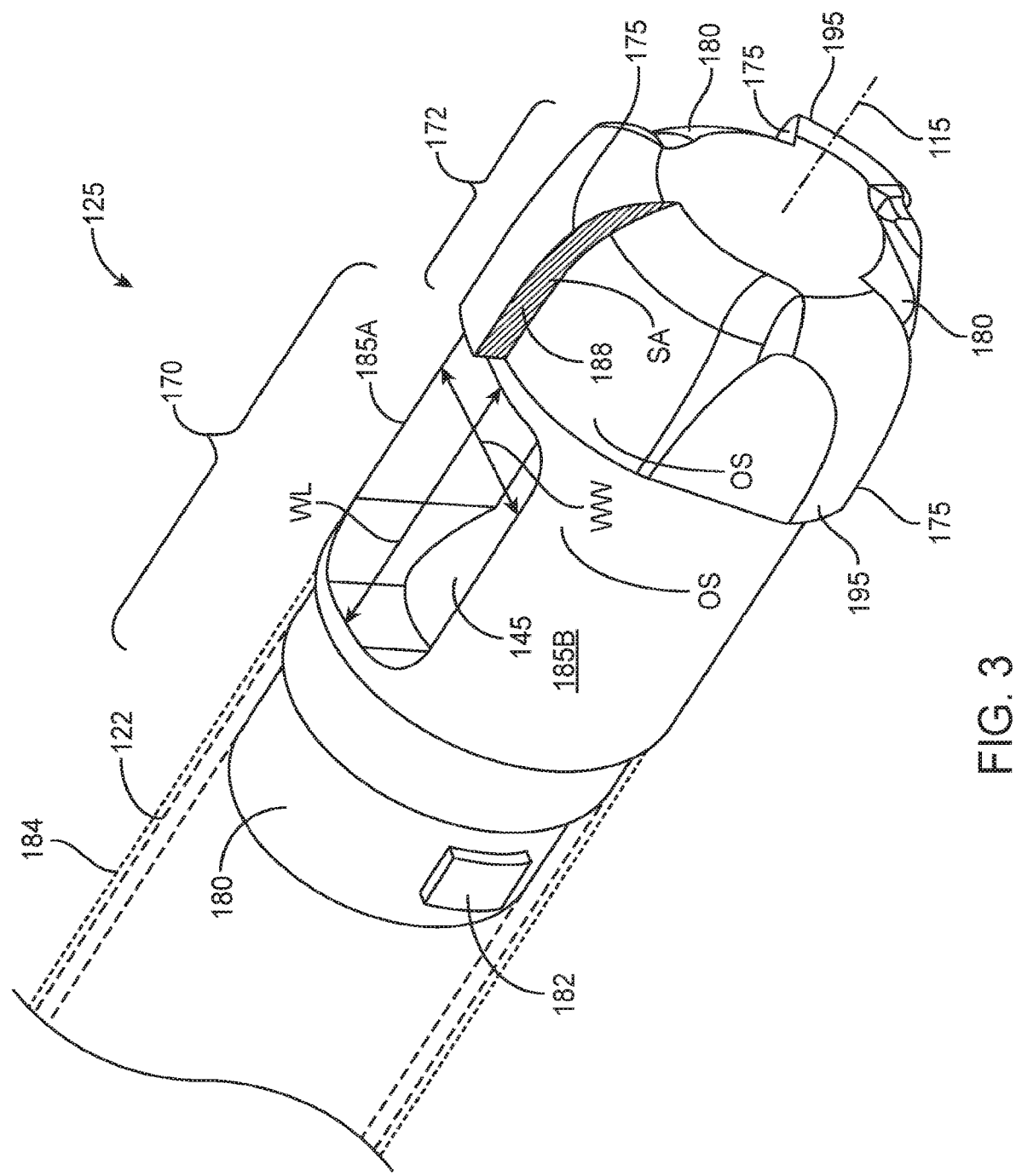
FIG. 3 is an enlarged perspective view of the ceramic cutting member of the arthroscopic cutter or shaver assembly of FIG. 1.
Figure 4A:
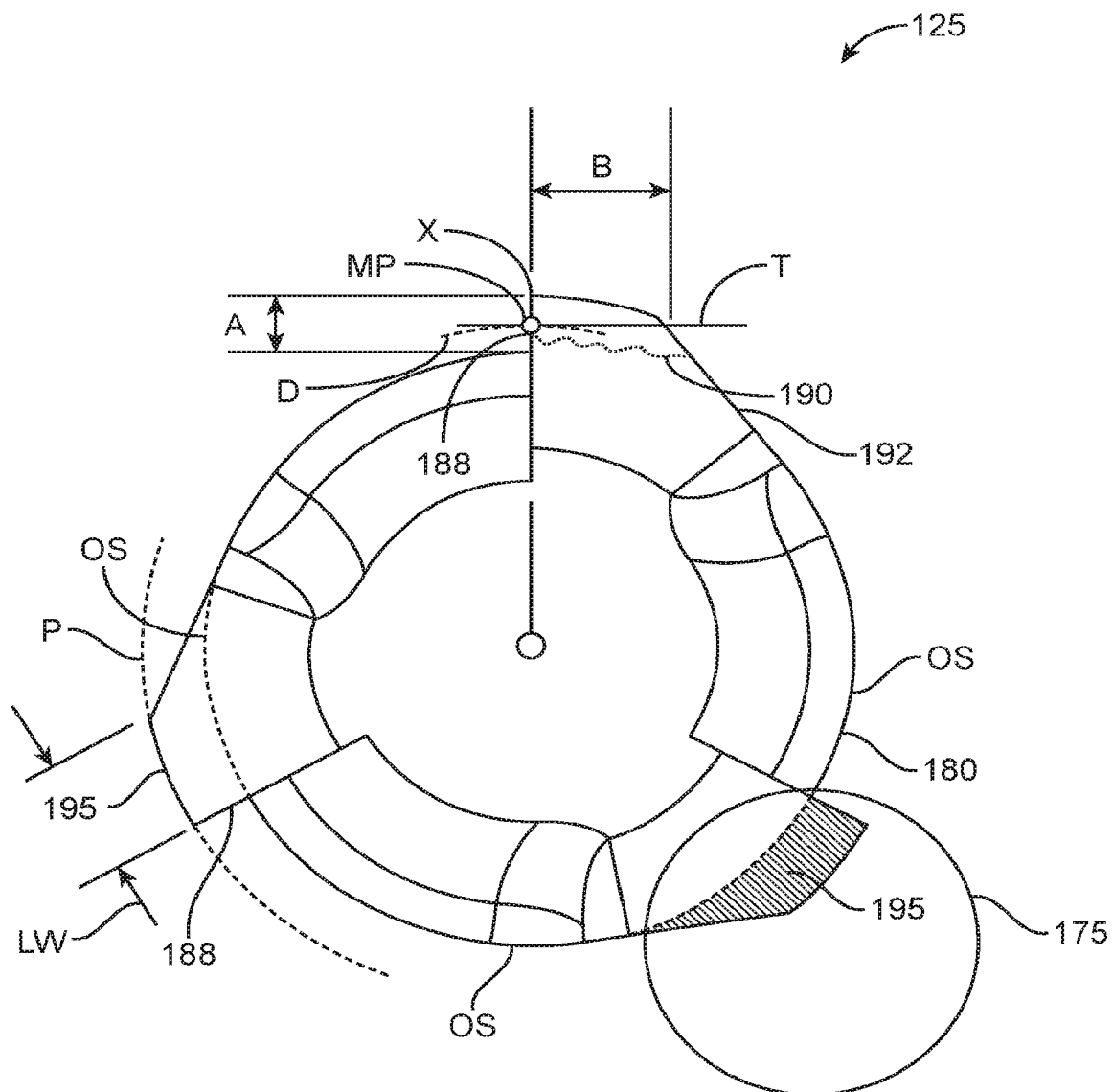
FIG. 4A is an enlarged end view of the ceramic cutting member of FIG. 3 corresponding to the invention showing several features including three non-helical, axis-aligned cutting edges, the cutting edge height and the cutting edge thickness.

Now referring to FIGS. 3 and 4A, the cutting member 125 comprises a ceramic body or monolith that is fabricated entirely of a technical ceramic material that has a very high hardness rating and a high fracture toughness rating, where "hardness" is measured on a Vickers scale and "fracture toughness" is measured in $MPam^{1/2}$. Fracture toughness refers to a property which describes the ability of a material containing a flaw or crack to resist further fracture and expresses a material's resistance to brittle fracture. The occurrence of flaws is not completely avoidable in the fabrication and processing of any components.

The authors evaluated technical ceramic materials and tested prototypes to determine which ceramics are best suited for the non-metal cutting member 125. When comparing the material hardness of the ceramic cutters of the invention to prior art metal cutters, it can easily be understood why typical stainless steel bone burrs are not optimal. Types 304 and 316 stainless steel have hardness ratings of 1.7 and 2.1, respectively, which is low and a fracture toughness ratings of 228 and 278, respectively, which is very high. Human bone has a hardness rating of 0.8, so a stainless steel cutter is only about 2.5 times harder than bone. The high fracture toughness of stainless steel results in ductile behavior which thus results in rapid cleaving and wear on sharp edges of a stainless steel cutting member. In contrast, technical ceramics materials have a hardness ranging from approximately 10 to 15, which is five to six times greater than stainless steel and which is 10 to 15 times harder than cortical bone. As a result, the sharp cutting edges of a ceramic remain sharp and will not become dull when cutting bone. The fracture toughness of suitable ceramics ranges from about 5 to 13 which is sufficient to prevent any fracturing or chipping of the ceramic cutting edges. The authors determined that a hardness-to-fracture toughness ratio ("hardness-toughness ratio") is a useful term for characterizing ceramic materials that are suitable for the invention as can be understood form the Chart A below, which lists hardness and fracture toughness of cortical bone, a 304 stainless steel, and several technical ceramic materials.

CHART A

| | Hardness (GPa) | Fracture Toughness ($MPam^{1/2}$) | Ratio Hardness to Fracture Toughness |
|---|---|---|---|
| Cortical bone | 0.8 | 12 | .07:1 |
| Stainless steel 304 | 2.1 | 228 | .01:1 |
| Yttria-stabilized zirconia (YTZP) | | | |
| YTZP 2000 (Superior Technical Ceramics) | 12.5 | 10 | 1.25:1 |
| YTZP 4000 (Superior Technical Ceramics) | 12.5 | 10 | 1.25:1 |
| YTZP (CoorsTek) | 13.0 | 13 | 1.00:1 |
| Magnesia stabilized zirconia (MSZ) | | | |
| Dura-Z ® (Superior Technical Ceramics) | 12.0 | 11 | 1.09:1 |
| MSZ 200 (CoorsTek) | 11.7 | 12 | 0.98:1 |
| Zirconia toughened alumina (ZTA) | | | |
| YTA-14 (Superior Technical Ceramics) | 14.0 | 5 | 2.80:1 |
| ZTA (CoorsTek) | 14.8 | 6 | 2.47:1 |
| Ceria stabilized zirconia | | | |
| CSZ (Superior Technical Ceramics) | 11.7 | 12 | 0.98:1 |
| Silicon Nitride | | | |
| SiN (Superior Technical Ceramics) | 15.0 | 6 | 2.50:1 |

As can be seen in Chart A, the hardness-toughness ratio for the listed ceramic materials ranges from 98× to 250× greater than the hardness-toughness ratio for stainless steel 304. In one aspect of the invention, a ceramic cutter for cutting hard tissue is provided that has a hardness-toughness ratio of at least 0.5:1, 0.8:1 or 1:1.

In one variation, the ceramic cutting member 125 of FIG. 3 is a form of zirconia. Zirconia-based ceramics have been widely used in dentistry and such materials were derived from structural ceramics used in aerospace and military armor. Such ceramics were modified to meet the additional requirements of biocompatibility and are doped with stabilizers to achieve high strength and fracture toughness. The types of ceramics used in the current invention have been used in dental implants, and technical details of such zirconia-based ceramics can be found in Volpato, et al., "Application of Zirconia in Dentistry: Biological, Mechanical and Optical Considerations", Chapter 17 in *Advances in Ceramics—Electric and Magnetic Ceramics, Bioceramics, Ceramics and Environment* (2011).

In one variation, the ceramic cutting member 125 of FIG. 3 is fabricated of an yttria-stabilized zirconia as is known in the field of technical ceramics, and can be provided by CoorsTek Inc., 16000 Table Mountain Pkwy., Golden, CO 80403 or Superior Technical Ceramics Corp., 600 Industrial Park Rd., St. Albans City, VT 05478. Other technical ceramics that may be uses consist of magnesia-stabilized zirconia, ceria-stabilized zirconia, zirconia toughened alumina and silicon nitride. In general, in one aspect of the invention, the monolithic ceramic cutting member 125 has a hardness rating of at least 8 Gpa (kg/mm$^2$). In another aspect of the invention, the ceramic cutting member 125 has a fracture toughness of at least 4 MPam$^{1/2}$.

The fabrication of such ceramics or monoblock components are known in the art of technical ceramics, but have not been used in the field of arthroscopic cutting or resecting devices. Ceramic part fabrication includes molding a part such as a cutting member 125 which is called "green" after release from a mold, then sintering or "firing" the molded green part at high temperatures over precise time intervals to transform the compressed ceramic powder into a ceramic monoblock which can provide the hardness range and fracture toughness range as described above. Injection molds for fabricating such ceramic cutting members are described in more detail below.

In FIG. 3, one variation of ceramic cutter 125 is shown which has a proximal shaft portion 170 and distal portion 172 which has cutting edges 175 extending radially outward from the outer surface OS of the cutting member. The shaft portion 170 has a reduced diameter section 180 that includes projecting elements 182 which engage receiving openings in the inner sleeve 122 for locking the cutting member 125 to the inner sleeve 122 (phantom view). A thin-wall polymeric sleeve 184, for example, heat shrink tubing is shown in phantom view in FIG. 3 extending over the inner sleeve 122 and the reduced diameter section 180 shaft portion 170 to provide a lubricious, dielectric outer layer covering the inner sleeve 122. In other variations, a ceramic cutting member 125 can be coupled to metal sleeve 122 by brazing, adhesives, threads or a combination thereof. Still referring to FIG. 3, the window 145 in the ceramic cutting member 125 can extend over a radial angle ranging between about 15° to 90° of the shaft portion 170. In a variation, the window 145 is provided with sharp outer edges 185A and 185B with a high radial rake angle for capturing bone chips and cutting soft tissue as will be described further below. Further, the bone chips or the resected soft tissue are moved or suctioned by the negative pressure source 160 through the window 145 and interior channel 126 (with diameter C) inthe ceramic member 125 and thereafter into the increased diameter lumen 128 of the inner sleeve 122 (see FIG. 1). The increase in diameter from channel 126 to inner sleeve lumen 128 is advantageous for providing a clog-free outflow pathway as any removed tissue that passes through the interior channel 126 in the ceramic cutting member 125 will be then entrained in fluid outflows in inner sleeve lumen 128.

As will be described next, a ceramic cutting member 125 of FIG. 3 corresponding to the invention has many unique features for functional purposes that distinguish its shape and configuration from prior art metal burrs or blades. After extensive testing, it has been found that an optimized ceramic cutting member 125 differs from typical metal burrs (see FIGS. 5A-5B) in several ways, including (i) the number of cutting edges, (ii) the height of the cutting edges, (iii) the thickness of the cutting edges (iv) the length and surface area of the cutting edges, and (v) the dimensions, configuration and location of the window in the cutting member. Further, the system of the invention uses higher rotational speeds than prior art systems for optimizing use of a ceramic cutter in cutting bone.

Figure 5A:
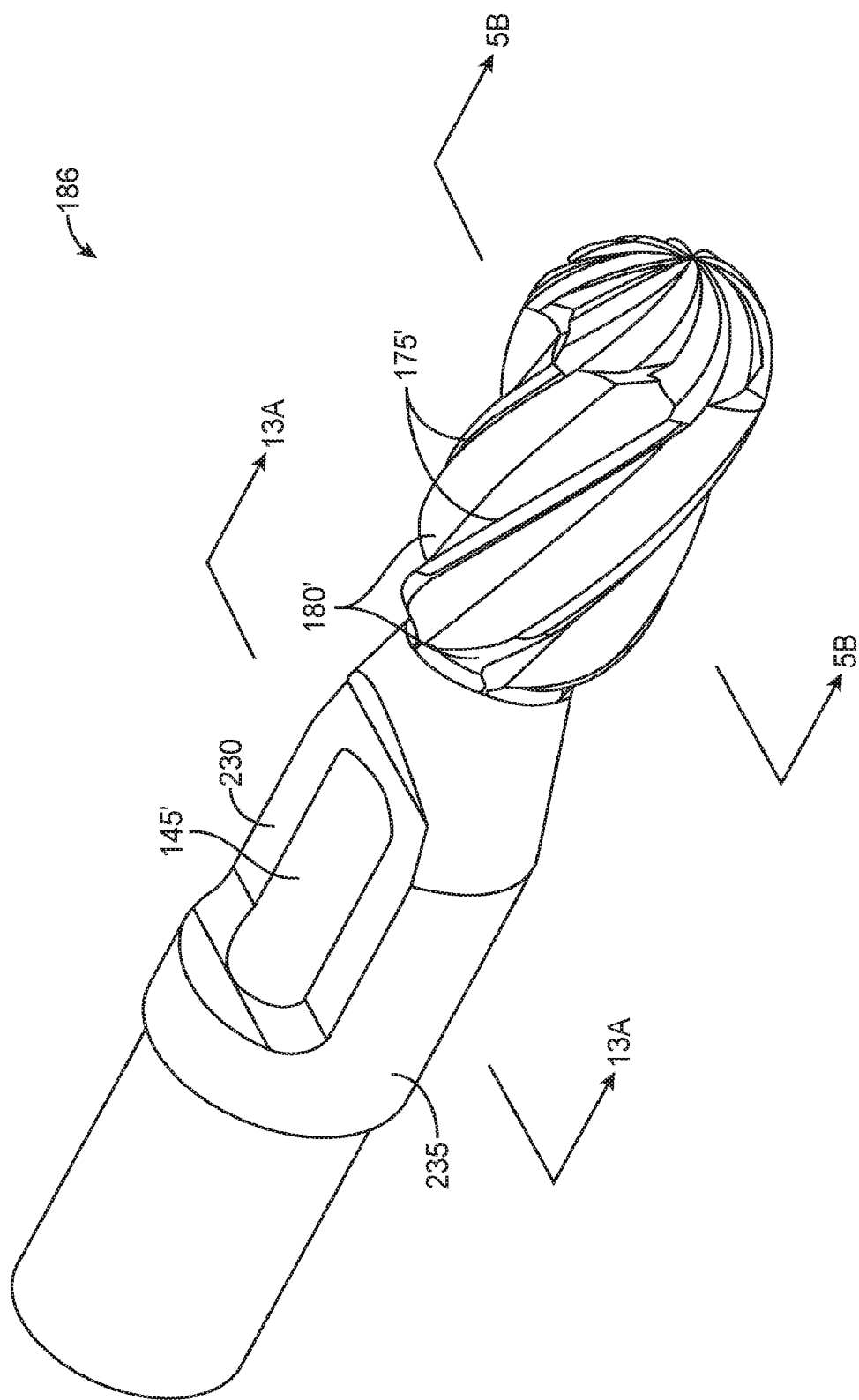
FIG. 5A is a perspective view of a prior art metal burr with eight elongate cutting edges and an aspiration window positioned proximal to the cutting edges.
Figure 5B:
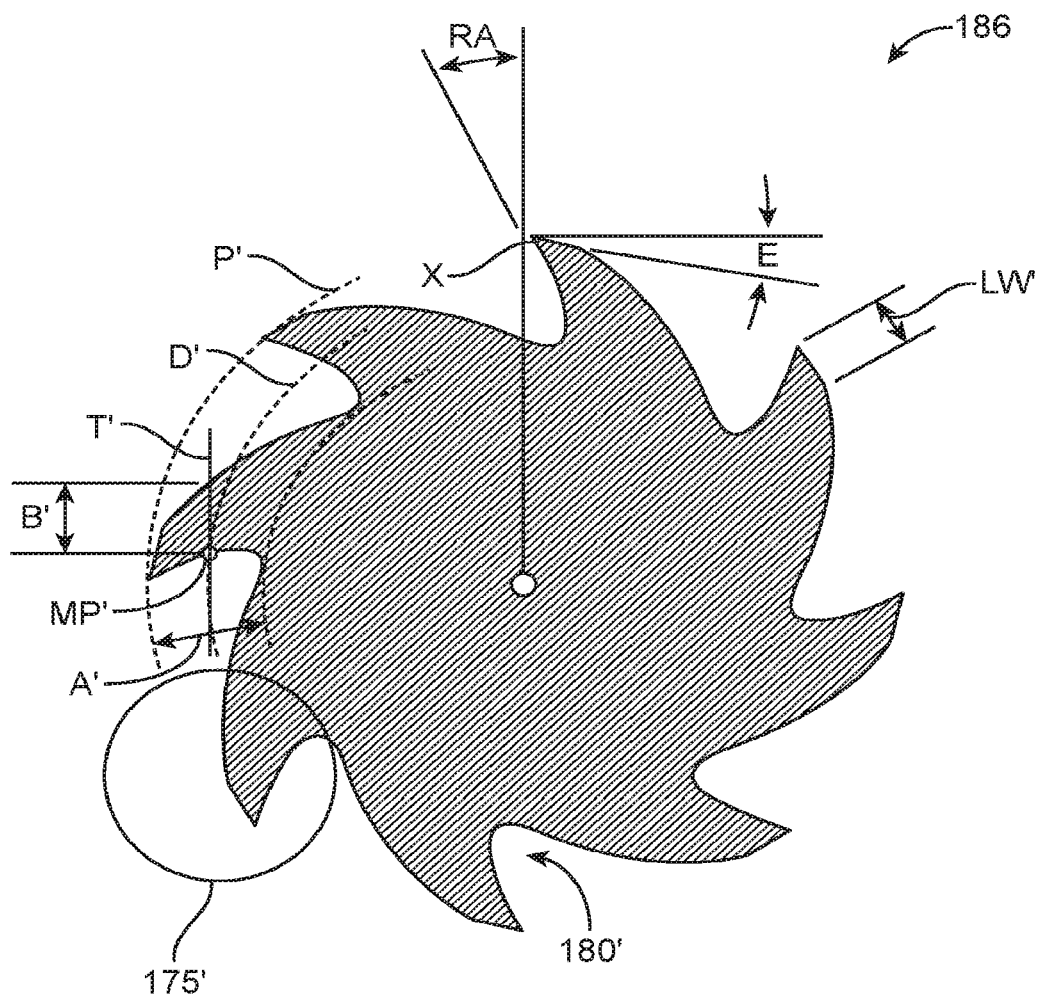
FIG. 5B is a cross-sectional view of the prior art metal burr of FIG. 5A taken along line 5B-5B of FIG. 5A showing the metal burr's radial rake angle, cutting edge height, cutting edge thickness, primary clearance angle and land width.

In the variation shown in FIGS. 3 and 4A, the ceramic cutting member or ceramic cutter body has three cutting edges 175 and three flutes 180 with the outer diameter or cutting edge periphery P being cylindrical and tapered or rounded in the distal direction. Metal shaver blades typically have six, eight or more cutting edges. FIGS. 5A-5B show a prior art metal shaver blade or burr 186 with eight cutting edges 175' and eight intermediate flutes 180'.

As can be seen in FIGS. 3 and 4A, the cutting edges 175 in ceramic cutting member 125 are typically non-helical or straight and aligned with longitudinal axis 115 to facilitate injection molding as will be described below. FIG. 4A shows the a cutting edge 175 as being defined as the hatched area that extends radially outward from the outer surface OS. In one aspect, it has been found that the ceramic cutter 125 (FIGS. 3 and 4A) with fewer cutting edges 175 than a metal burr is optimal for bone cutting. Further, an optimal ceramic cutter has cutting edges with a height A which is much less than a cutting edge height in a typical metal burr (see FIGS. 5A-5B). The ceramic cutting member 125 in FIG. 4A, for example, is configured with three cutting edges 175. The reduced cutting edge height A allows for a smoother cutting, less chattering, and improved tactile feedback to the user's hand during the bone cutting process. In addition, a ceramic cutting member with fewer cutting edges 175 and reduced cutting edge height A can be combined with higher rotational speeds than prior art metal burrs to cut bone at a faster rate (in terms of grams/min). The system of FIGS. 1 and 2 corresponding to the invention operates at up to 20,000 RPM and in one variation operates at 16,500 RPM for bone cutting. Commercially available metal burrs typically operate at a maximum of 12,000 RPM. If commercially available metal burrs were operated at higher RPMs, the metal edges would become dull much more rapidly.

Figure 4B:
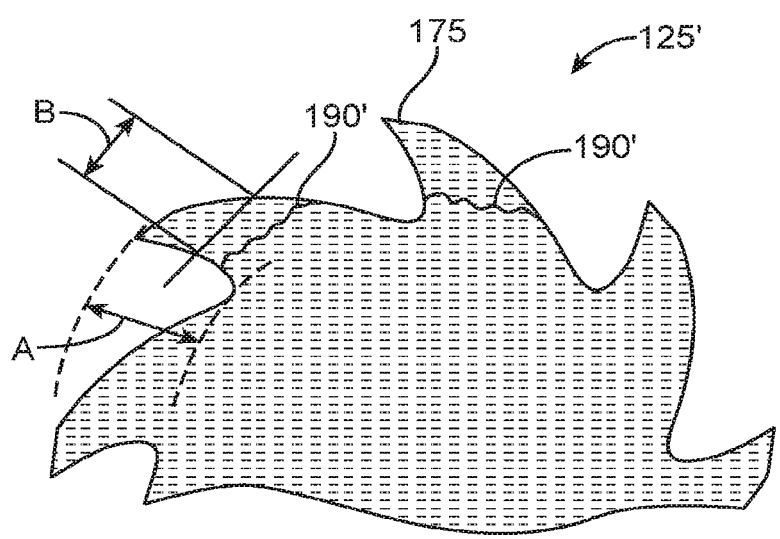
FIG. 4B is a sectional view of a hypothetical ceramic cutting member with a high cutting edge height and a low cutting edge thickness which illustrates how the cutting edges would fracture.

Referring to FIGS. 3-4A, a variation of ceramic cutting member 125 has three cutting edges 175, however other variations for bone cutting can have from 2 to 6 cutting edges. In another aspect of the invention relating to the cutting edges 175, the reduced number of cutting edges allows for much higher strength cutting edges in a ceramic body. It has been found that ceramic cutting edges 175 benefit from substantial bulk or thickness B (see FIG. 4A) behind the cutting faces 188 which can prevent a potential fracture in the ceramic, for example, along line 190 indicated in FIG. 4A. FIG. 5B shows a prior art metal cutting edge 175' which has relatively little bulk or thickness B' compared to the ceramic cutting edge thickness B of FIG. 4A. Referring to FIG. 4A, an appropriate manner of characterizing the thickness or bulk of a cutting edge 175 is to define the cutting edge thickness B as a dimension along a tangent T to a diameter D at a midpoint MP from a cutting face 188 to the back side 192 of the cutting edge 175 which is a surface of the adjacent flute 180. As can be seen in the prior art metal cutter of FIG. 5B, the prior art thickness B' of the cutting edge 175' along tangent T' of diameter D' at midpoint MP' of the cutting edge is small in relation to height A' of the cutting edge due to the ductile, high fracture resistance of metal as opposed to a ceramic (see Chart A above). FIG. 4B illustrates a hypothetical cutting member 125' that fabricated of a ceramic with the cutting edge height A and thickness B of a prior art metal burr as in FIGS. 5A-5B. In such a ceramic cutter 125' as depicted in FIG. 4B, the cutting edges 175 would fracture along line 190' due to the lack of cutting edge thickness B which equates with strength or fracture resistance. Referring back to the prior art metal burr embodiment of FIG. 5B, the ratio of edge thickness B' to edge height A' is much less than 1:1. In the cutting member 125 corresponding to the invention in FIG. 4A, such a ceramic cutting member has a cutting edge thickness B to height A ratio of greater than 1.5, and more often greater than 2:1.

In general, an arthroscopic cutter corresponding to the invention comprises a ceramic body with a plurality of cutting edges 175 and intermediate flutes 180 wherein each cutting edge defines a cutting edge height A measured from an outer cutting edge diameter P to a flute bottom or surface OS, where the ratio of the cutting edge thickness to the cutting edge height is at least 1.5:1 when the cutting edge thickness is measured along a tangent to a midpoint of the cutting face 188 to the adjacent flute. In another variation, the ratio of the cutting edge thickness to the cutting face height is at least 2:1.

In another aspect, the cutting edge height A relative to the outer cutting edge diameter P is small compared to prior art metal burrs such as illustrated in FIGS. 5A-5B. In the variation of the invention shown in FIGS. 3 and 4A, the cutting edge height A is 0.02 inch which is less than 10% of the outer periphery diameter P of the cutting member. In general, the ratio of the cutting edge height A to the periphery diameter P is 0.2:1 or less, or often such a ratio is 0.1:1 or less.

Figure 6:
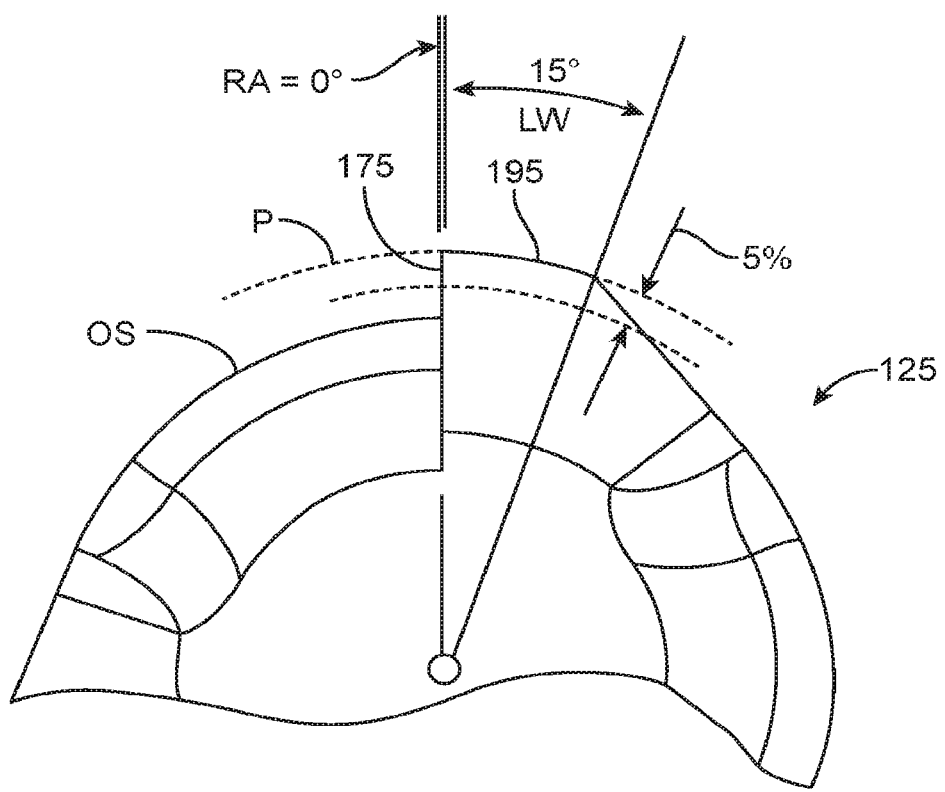
FIG. 6 is an end view of a portion of the ceramic cutting member of FIGS. 3 and 4A showing the radial rake angle of the cutting edges and a means for defining the thickness of the cutting edges.

Another way to define the bulk or thickness of the cutting edges 175 of ceramic cutter 125 (FIGS. 3-4) compared to a prior art metal burr as in FIGS. 5A-5B is to consider the primary relief angle of the cutting edges. Referring to FIG. 5B, in standard nomenclature for rotary cutters, the primary relief angle E is the angle of the outer surface just behind the apex X of the cutting edge 175'. In metal burrs, there is typically a relief angle of a 2° to 10°, which allows the apex X to engage targeted material even after the apex X becomes dull. It can be easily understood that as an apex X of a metal cutting edge becomes dull, a relief angle is needed. Otherwise, the rotating cutter could simply ride on the backside of the cutting edge 175' over the targeted tissue. In contrast, turning to FIG. 6, the cutting edges 175 of the ceramic cutter 125 of FIGS. 3, 4A and 6 have no primary relief angle at all. Of particular interest, it has been found that since the ceramic cutting edges 175 do not become dull, there is no need (or performance gain) by providing a primary relief angle. Instead, in a ceramic cutter 125 corresponding to the invention, the lands 195 have a lands width LW at the outer periphery diameter P than extends over a radial angle of greater than 10°, and in the variation of FIGS. 3 and 6, greater than 15°. The scope of the invention includes the option of providing some primary clearance, for example a clearance angle of up to 5°. Alternatively, the amount of clearance can be better defined by the "radial" depth of the clearance, as in a percentage of the periphery diameter P of the ceramic cutter 125. In general, referring to FIG. 6, an arthroscopic cutter corresponding to the invention comprises a ceramic body with a plurality of cutting edges 175 and intermediate flutes 180 wherein each cutting edge 175 has lands 195 with a clearance of less than 5% of the outer periphery diameter P at a radial angle of 15° behind the apex X of the cutting edge 175.

In another aspect of the invention referring to FIG. 4A, the ceramic cutter 125 has cutting edges 175 with a 0° radial rake angle RA whereas metal burrs always have a substantial positive radial rake angle. The radial rake angle RA' of a prior art metal burr of FIG. 5B can range from about 2° to 15°. Positive rake angles are needed in metal burrs or cutters to make such cutters function somewhat effectively as the apex X of the cutting edge dulls rapidly. Of particular interest, referring to FIG. 4, it has been found that an optimal radial rake angle RA of a ceramic cutter 125 is 0°. In other variations, the radial rake angle RA of a ceramic cutter 125 can range from about −5° up to about +10°.

Figure 7A:
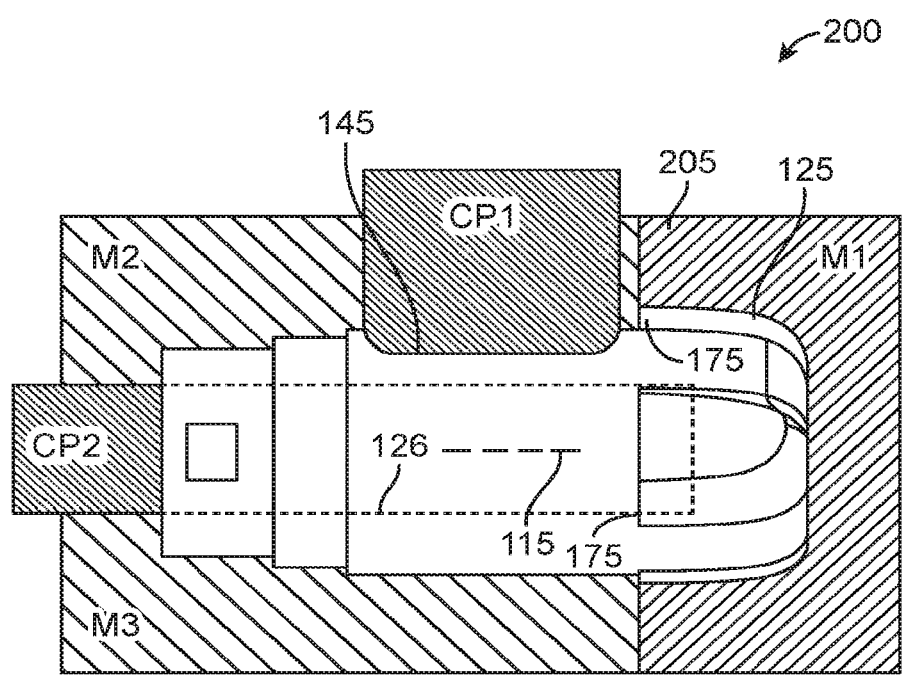
FIG. 7A is a cut-away sectional schematic view of a multi-component ceramic injection mold illustrating a method of fabricating a ceramic cutting member (shown in a side view) with core pins configured to form the window and the interior channel in the cutting member.
Figure 7B:
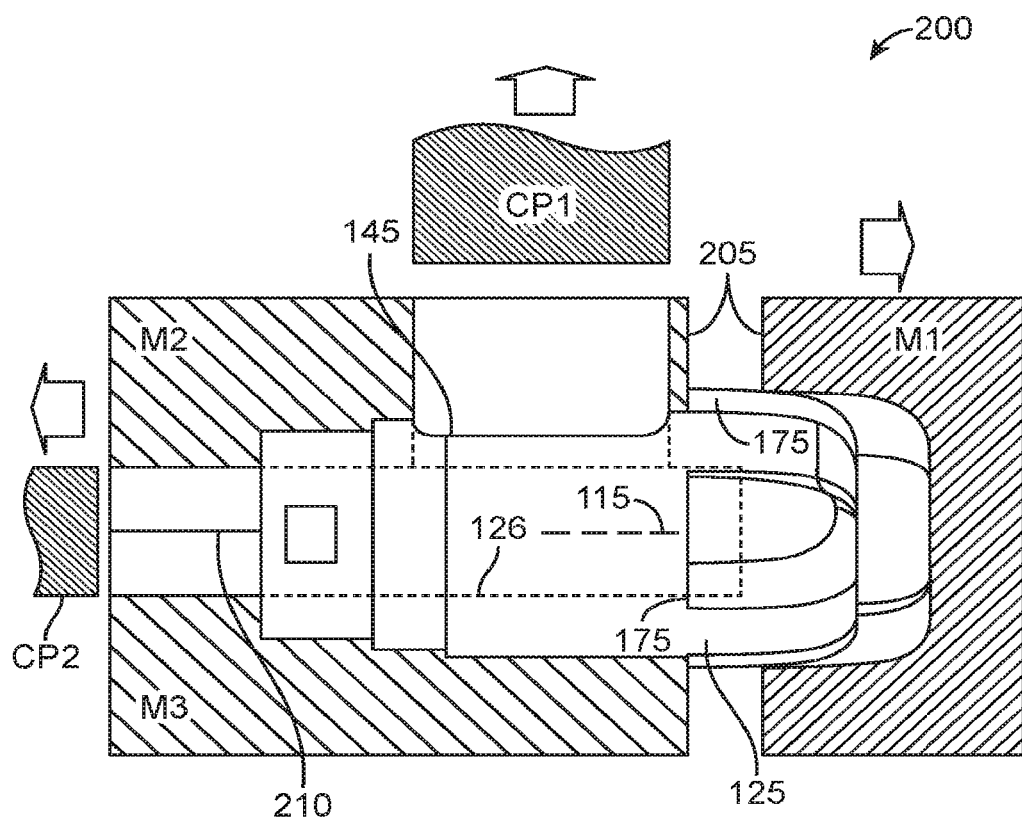
FIG. 7B another cut-away view of the multi-component ceramic injection mold of FIG. 7A showing schematically the first and second core pins after being removed and a first mold component being moved in alignment with the axis of the cutting member to release the distal cutting edge portion from the mold.
Figure 7C:
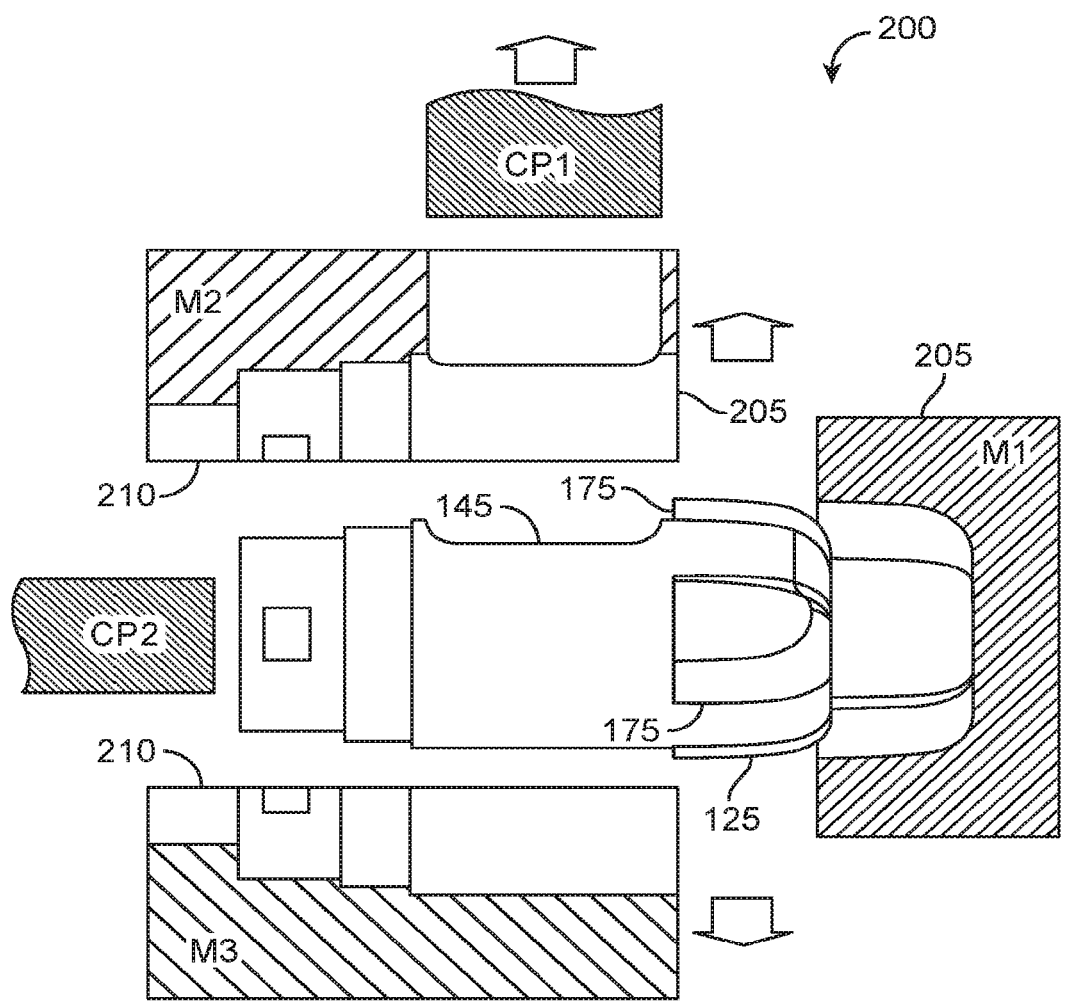
FIG. 7C another cut-away view of the multi-component ceramic injection mold of FIGS. 7A-7B showing schematically second and third mold components being moved away from the axis of the cutting member to release the proximal shaft portion from the mold.

In another aspect of the invention as described above referring to FIGS. 3 and 4A, the ceramic cutter 125 has cutting edges 175 that are non-helical and aligned with the longitudinal axis 115 of the cutting member 125. In contrast, typical prior art metal burrs as shown in FIGS. 5A-5B have helical cutting edges. This aspect of the ceramic cutting member 125 of FIGS. 3-4A that relates to non-helical cutting edges facilitates a method of injection molding the ceramic body 125 with a three-component parting mold 200 as shown in FIGS. 7A-7C. FIG. 7A is a schematic sectional view of a parting mold with three parting mold components M1, M2 and M3 and two core pins CP1 and CP2. The mold 200 parts along lines 205 and 210 as can be seen in FIGS. 7B and 7C. FIG. 7B schematically depicts several steps of releasing the green ceramic cutting member 125 from mold 200. Of particular interest, the mold component M1 is adapted to part from the other components M2 and M3 by axial movement away form distal portion 172 and cutting edges 175 of ceramic cutting member 125 aligned with the longitudinal axis 115 as can be understood from FIGS. 7A and 7B. It is for this reason that cutting edges 175 are straight and aligned with the ceramic body's longitudinal axis 115. In other words, the axially-aligned cutting edges 175 are aligned with the parting direction (the longitudinal axis 115) of mold component M1 (FIG. 7B). As can be understood from the FIGS. 7A-7B, the cutting edges 175 can also have a positive rake angle of up to 5° or more (see FIG. 4A) and the mold component M1 then can still release from the molded green cutting member body 125.

FIG. 7B further shows other steps of the mold release which includes withdrawal of core pin CP1 in a direction orthogonal to axis 115 to provide the window 145 in the ceramic cutter 125. This design of the mold 200 and core pin CP1 is configured to form the window edges 185A and 185B with high positive radial rake angles (see FIGS. 3 and 10) as will be discussed further below. Also, FIG. 7B shows withdrawal of core pin CP2 in the axial direction to provide axial inner channel 126 in the ceramic cutting member 125.

FIG. 7C shows another step of the mold release wherein the mold component M2 is moved away from the shaft portion 170 of cutting member 125 in a direction orthogonal to the longitudinal axis. Further, the mold component M3 is moved relative to the shaft portion 170 of the cutting member to thereby release green cutting member 125 from the mold 200. A typical mold 200 will also have ejector pins for pushing the green ceramic cutting member 125 from the mold. Such ejector pins are not shown in the drawings for convenience.

Figure 8A:
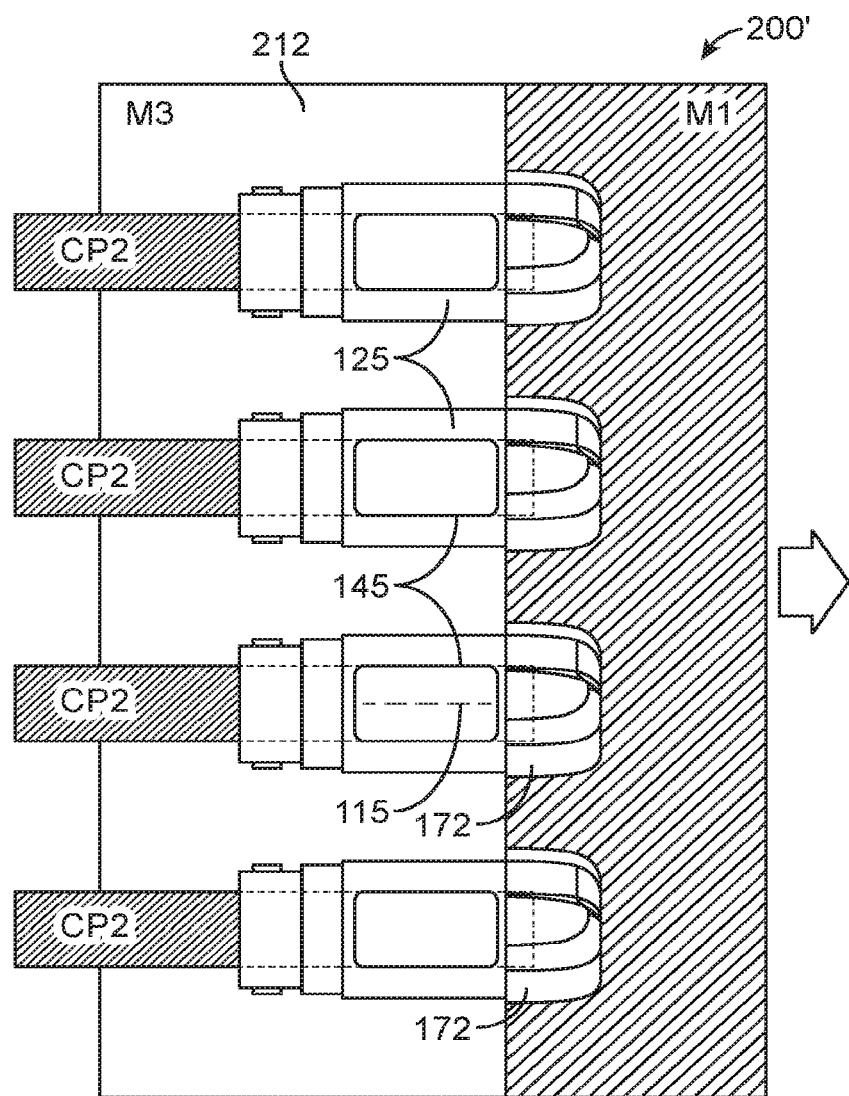
FIG. 8A is a cut-away view of a multi-cavity ceramic injection mold for molding a plurality of cutting members that shows cutting members in a top view, with the mold operating similar to the single cavity mold of FIGS. 7A-7C.
Figure 8B:
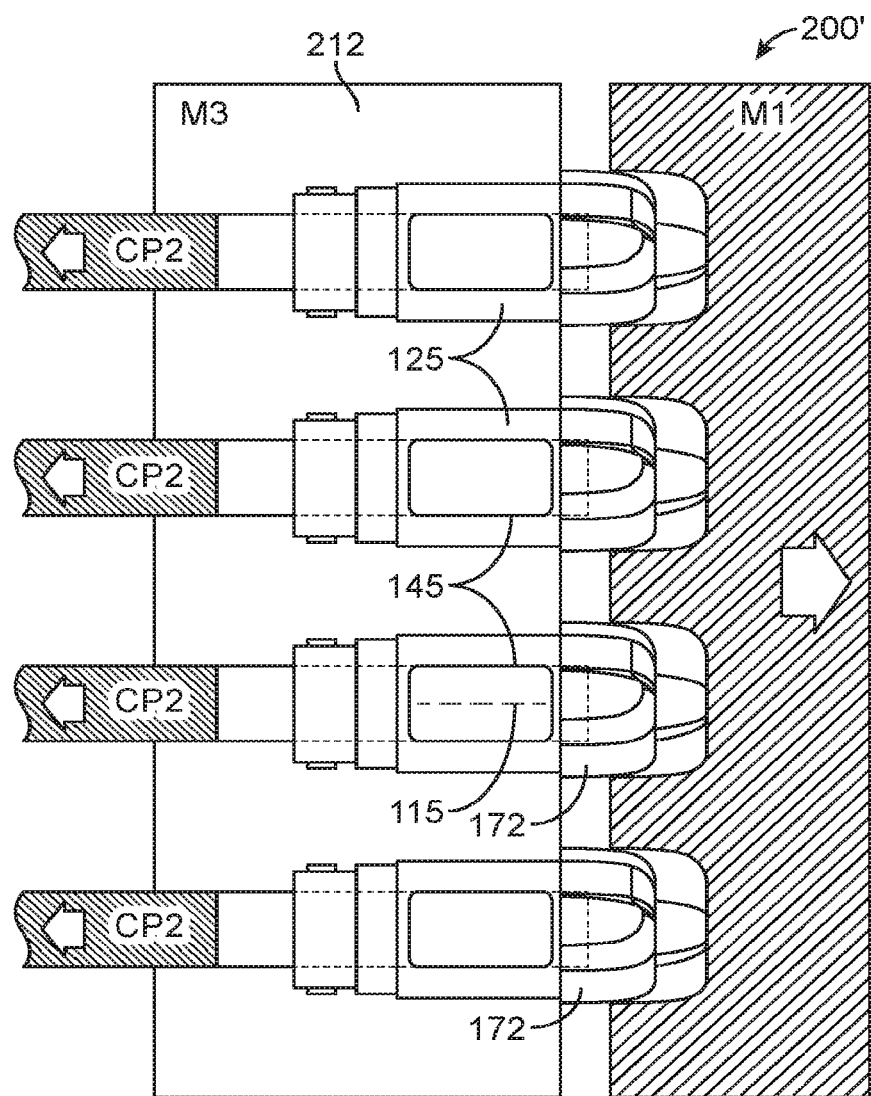
FIG. 8B is another cut-away view of the multi-cavity mold of FIG. 8A showing a core ping being removed and a mold component being moved in alignment with the axis of the cutting member to release the distal cutting edge portion from the mold similar to that of FIG. 7B.

In another aspect of the invention referring to FIGS. 8A-8B, a multi-cavity ceramic injection mold 200' can be fabricated to mold a plurality of cutting members 125. The multi-cavity mold incorporates the mold release parting lines and release directions described above as shown in FIGS. 7A-7C. It can be seen that FIGS. 7A-7B show the single-cavity mold 200 in a "side view" relative to the cutting member 125 whereas FIGS. 8A-8B show the mold 200' in a "top view" with respect to the green cutting members 125. FIG. 8A is a sectional view through an exemplary four-cavity mold 200' although such a mold can have from 2 to 16 or more mold cavities. In FIG. 8A, the mold component M2 and core pin CP1 (see FIGS. 7A-7B)

are removed so the surface 212 of mold component M3 is shown with a sectional view of mold component M1. FIG. 8A shows core pins CP2 in sectional view with the cutting member 125 in an elevational top view. FIG. 8B shows how mold component M1 can be moved axially in alignment with the axis 115 of the cutting members 125 to release the mold component from the distal portion 172 of a plurality of ceramic cutting members 125 as described previously. Core pins CP2 are shown in a retracted position in FIG. 8B.

In general, an arthroscopic cutting member configured for ceramic injection molding corresponding to the invention comprises a cutting member 125 having a longitudinal axis 115 and a plurality of cutting edges 175 extending radially outwardly from an outer surface OS, wherein the cutting member is formed from a wear-resistant ceramic material and wherein each cutting edge is non-helical and aligned with the longitudinal axis to enable ceramic injection molding with a multi-component parting mold (see FIGS. 3, 4A and 7A-7C).

Figure 9:
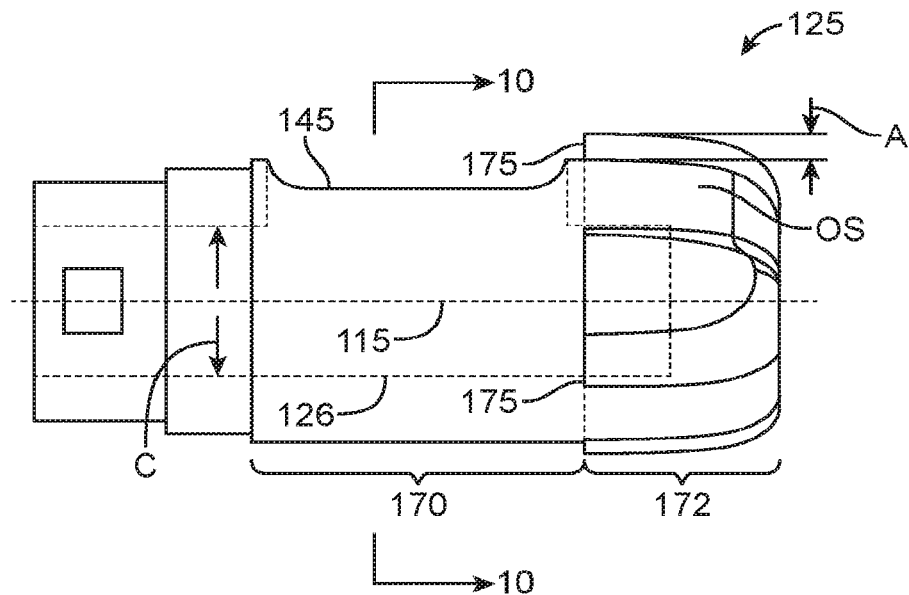
FIG. 9 is a side elevation view of the ceramic cutting member of FIGS. 3 and 4A showing the dimension of the interior channel.
Figure 10:
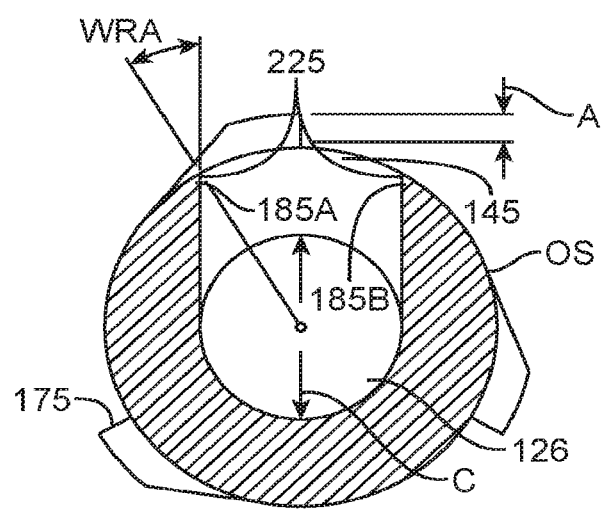
FIG. 10 is a sectional view of the cutting member of FIG. 9 taken along line 10-10 of FIG. 9 showing another view of the interior channel and the window having longitudinal edges that have a sharp apex and a high positive radial rake angle.
Figure 11:
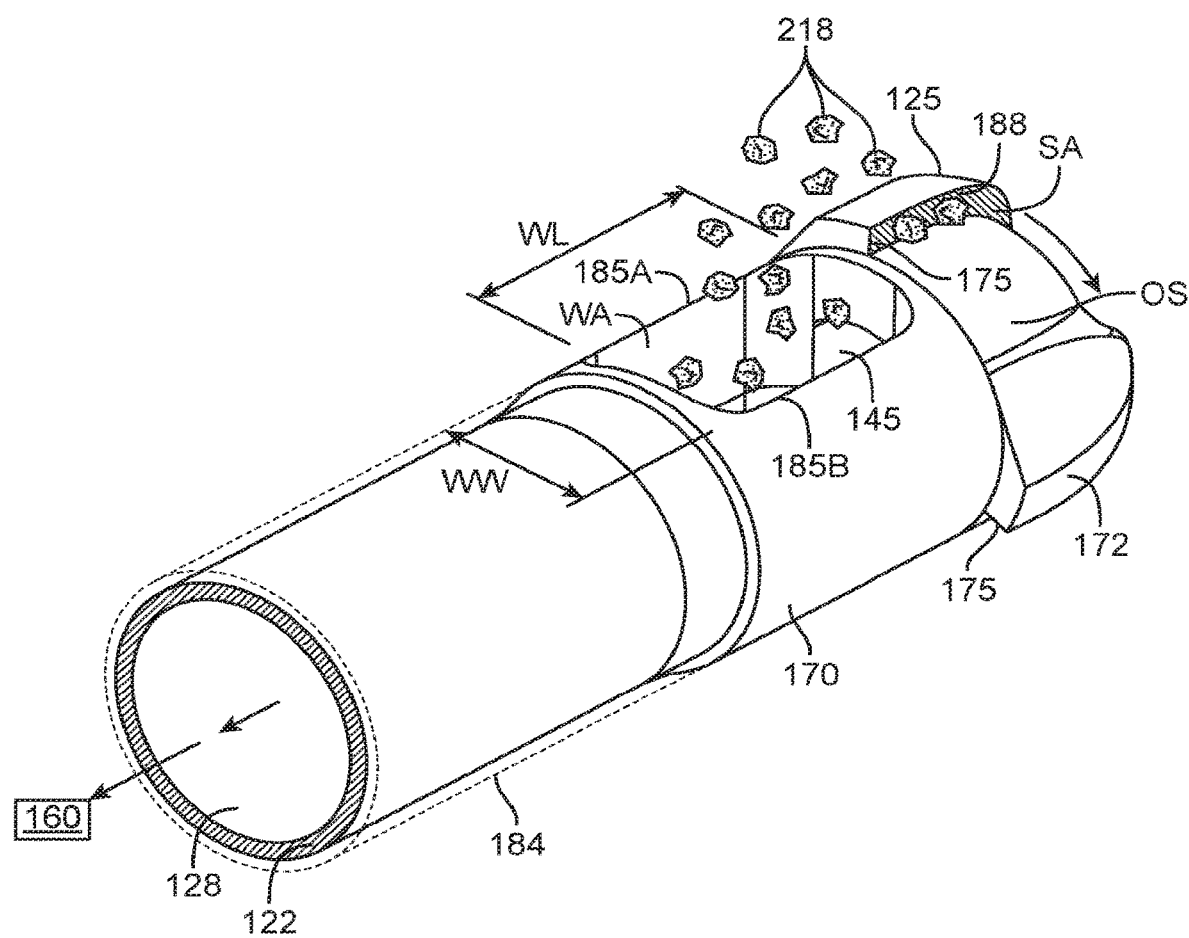
FIG. 11 is a perspective view of the cutting member of FIGS. 3, 4A and 9 schematically showing the cutting of bone chips and the resulting cross-section of such bone chips.

Now referring to FIGS. 9 and 10, it can be seen that the cutting edge height A (FIG. 4A) and the cutting face surface area SA (see hatched area in FIGS. 3 and 11) relative to the cutter periphery diameter P is substantially less than that of the prior art metal burr as shown in FIGS. 5A-5B. As described above, the reduced height A of a ceramic cutting edge 175 (FIG. 4A) when combined with the non-dulling aspect of the ceramic edge 175 and the higher rotational speed allows for cutting bone at a faster rate than prior art metal burrs. As can be understood intuitively, the cutting edge height A and surface area SA (FIGS. 3 and 11) are the key factors that determine the size of bone chips and the cutting rate. In general, referring to FIG. 11, the size of bone chips 218 typically is no larger in cross-section than the height A of cutting edge 175 as the elongated cutting surface does not result in elongated bone chips. Rather, the cross-sectional dimensions of bone chips 218 are essentially limited to the potential cutting depth (edge height A). Any elongated cut bone chips will fracture into smaller chips as schematically depicted in FIG. 11. Since the non-dulling ceramic cutter 125 cuts bone at a very fast rate, there is a complementary need for fast, efficient bone chip evacuation through the window 145. As outlined above, bone chips 218 are evacuated through window 145 into interior channel 126 of ceramic cutting member 125 (FIG. 9) and the lumen 128 of the inner sleeve 122 (FIG. 11) that communicates with negative pressure source 160. The bone chips 218 are collected in a collection reservoir 220 (see FIG. 2).

In one aspect of the invention, referring to FIGS. 3, 10 and 11, the width WW of the window 145 is critically important for the efficient extraction of bone chips, with the window length WL being a suitable length, for example, at least equal to the window width WW. With the cutting member 125 rotating at 16,500 RPM, it has been found that window width WW is most critical in capturing and then suctioning bone chips 218 away from the treatment site. In the variation shown in FIGS. 10 and 11, the ratio between the width WW of window 145 relative to the cutting edge height A is at least 5:1 and often greater than 6:1. This allows for bone chips to be rapidly suctioned into and through the window 145 and through interior passageway 126 of cutting member 125 in response to the negative pressure source 160. Further, the diameter C of interior channel is large relative to the cutting edge height A (FIG. 10) as will be described further below.

In another aspect of the invention, referring to FIGS. 10 and 11, the volume of bone chips 218 resulting from rotation of the cutting member 125 is a function of both the height A and length L of the cutting edges 175. In other words, the surface area SA of a cutting edge face 188 or faces and the rotational speed are directly correlated to the cutting rate in grams/minute of bone removal. It can be easily understood that it is the cutting edge surface area SA that interfaces with bone and thus cuts a corresponding volume of bone chips. In this regard, the window area WA relative to a cutting edge surface area SA is an important functional metric for a ceramic cutter, and in the variation of FIGS. 9-11, the ratio of the window area WA to a cutting edge surface area SA is greater than 8:1. In a typical prior art metal burr as shown in FIG. 5A, the window to edge surface area ratio is much less, for example about 2:1. In another metric, if the aggregate surface area of all cutting edges were considered, a ceramic cutter with only 2 or 3 cutting edges would have a far higher ratio of window to cutting surface than that of a typical metal burr with 6 to 8 or more cutting edges.

Referring to FIGS. 9, 10 and 11, in another aspect of the invention relating to extracting bone chips 218 from the treatment site, it can be seen that the diameter C of the interior channel 126 in the ceramic cutting member 125 is substantially larger than height A of the cutting edge 175. In one variation of FIGS. 9-10, the ratio of the inner channel diameter C to the cutting edge height A is about 6:1, and the scope of the invention includes such a ratio being at least 2:1, at least 4:1 or at least 6:1. In general, the cutting member comprises a wear resistant ceramic body carried by an elongate shaft, wherein the ceramic body has a plurality of cutting edges and flutes intermediate the cutting edges, and a window 145 in the cutting member open to an interior channel 126 that communicates with a lumen 128 in the shaft 110 wherein the ratio of the diameter C of the interior channel to the height A of the cutting faces is at least 2:1. In this variation, each cutting edge 175 defines a cutting edge height A or face height measured from an outer cutting edge periphery diameter P to a flute bottom diameter or outer surface OS.

Referring to FIGS. 3, 9 and 10, in another aspect of the invention, the diameter C of the interior channel 125 of the cutting member 125 is large relative to the outer periphery diameter P. The ratio of the interior channel diameter C to the outer periphery diameter P of the cutting edges 125 is at least 0.4:1. In the variation of FIGS. 3, 9 and 10, the ratio is 0.048:1. In general, a ceramic cutter differs from a metal burr in that the height A of the cutting edges is small relative to the outer periphery diameter P and the interior channel diameter C for extracting bone chips is large relative to the outer periphery P. Thus, in one aspect of the invention, a cutting member has a longitudinal axis and a plurality of cutting edges extending radially outwardly from an outer surface OS thereof, a window 145 through the outer surface OS communicating with a longitudinal interior channel 126 therein, wherein the ratio of the outer surface diameter OS to the outer periphery diameter P of the cutting edges 125 is at least 0.75:1, and wherein the ratio of the channel diameter C to the outer diameter P of the cutting edges 125 is at least 0.4:1.

Figure 12A:
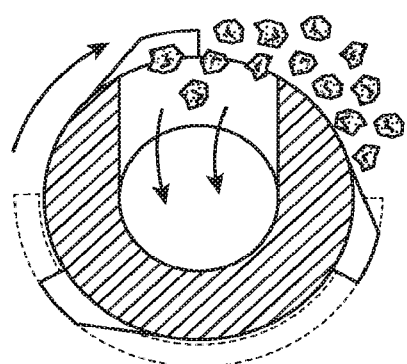
FIG. 12A is a sectional view of the shaft portion and window of the cutting member of FIGS. 3, 4A and 9 schematically rotating in relation to bone chips.
Figure 12B:
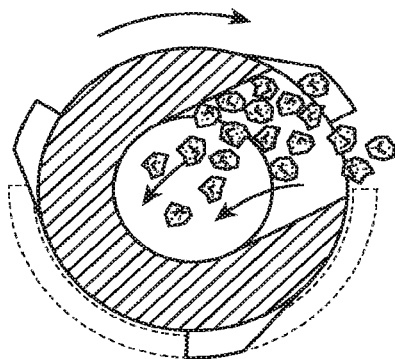
FIG. 12B is a sectional view of the cutting member window of FIG. 12A after further rotation wherein the window's sharp apex and a high positive radial rake angle capture bone chips.
Figure 13A:
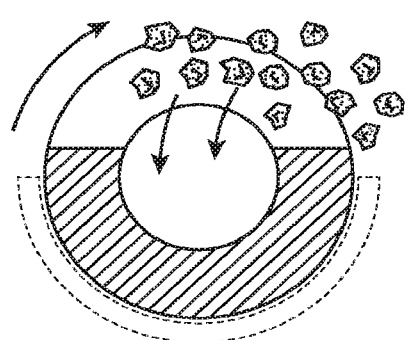
FIG. 13A is a sectional view of the window of the prior art metal burr of FIG. 5A taken along line 13A-13A of FIG. 5A schematically rotating in relation to bone chips.
Figure 13B:
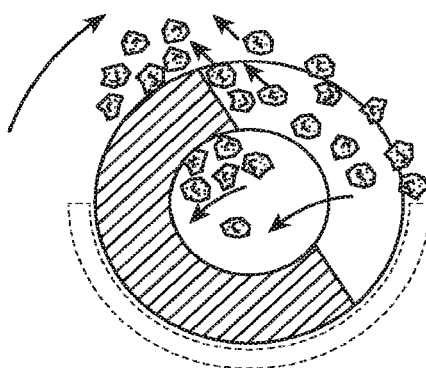
FIG. 13B is another view of the prior art metal burr window of FIG. 13A after further rotation wherein the window's negative radial rake angle does not facilitate the capture bone chips.

In another aspect of the invention, referring to FIGS. 12A-12B, the window 145 is configured to assist in the extraction of bone chips 218 during high-speed rotation in the cut-out 144 region of outer sleeve 120. As can be seen in FIG. 10, each window edge 185A, 185B has a sharp apex 225 and more importantly has a radial window rake angle WRA is non-zero and positive, (see FIG. 10) and typically ranges from about 15° to 45° to capture bone chips 218 as the shaft portion 170 and window 145 rotate. In FIGS. 12A-12B, the high radial rake angle WRA (see FIG. 10) of the window edge 185A and apex 225 are shown in assisting in the capture bone chips 218 in window 145 under the negative pressure in the window 145 provided by the negative pressure source 160. In FIG. 12B, the sectional view schematically depicts that the outer edge or apex 225 of the window 145 can strike and deflect bone chips 218 inwardly into the interior channel 126. In contrast, FIGS. 13A-13B illustrates a sectional view of the metal burr window 145' of FIG. 5A under high-speed rotation. The prior art metal burr of FIG. 5A does not have a positive window radial rake angle, and in fact has a negative radial rate angle WRA' (FIG. 13A), so that bone chips 218 are struck by the window face 230 instead of a sharp outer edge with a positive rake angle as in the ceramic cutter 125 of FIGS. 12A-12B. In the prior art metal burr of FIGS. 5A and 13A-13B, the substantially negative radial rake angle of window face 230 is fabricated simply by grinding flat faces on the metal sleeve 235 in which the window 230 is formed.

In another aspect of the invention, the ceramic cutting member 125 of FIGS. 3, 9, 10 and 11 has the distal edge of the window 145 positioned very close to the proximal end of the cutting edges 175, for example less than 0.10 inch or less than 0.05 inch. In prior metal burrs such as in the burr 186 of FIG. 5A, the aspiration window 145' is necessarily positioned axially away from the cutting edges 175' since the metal sleeve 235 need a distal portion configured for welding to the portion carrying the cutting edges.

Chart B below describes the various dimensions and ratios of the ceramic cutter 125 of FIGS. 3, 4A, 9 and 10 that were described above. This is one variation of a ceramic cutter 125 that has been tested extensively and operated at 16,500 RPM to cut bone.

CHART B

| | | | |
|---|---|---|---|
| A | Cutting Edge Height | 0.0205 | inch |
| B | Cutting Edge Thickness | 0.0450 | inch |
| P | Periphery Diameter | 0.2590 | inch |
| OS | Outer Surface Diameter (Shaft Portion) | 0.2180 | inch |
| C | Interior Channel Diameter | 0.1250 | inch |
| L | Cutting Edge Length | 0.1378 | inch |
| SA | Cutting Edge Surface Area | 0.0031 | sq. in. |
| PA | Periphery Surface Area | 0.1400 | sq. in. |
| RA | Radial Rake Angle-Cutting Edges | 0 | o |
| WRA | Radial Rake Angle-Window | 35 | o |
| WW | Window Width | 0.1250 | inch |
| WL | Window Length | 0.2062 | inch |
| WA | Window Area | 0.0247 | sq. in. |
| Ratio-Cutting Edge Height to Periphery Diameter | | 0.08:1 | |
| Ratio-Window Width to Cutting Edge Height | | 6.1:1 | |
| Ratio-Window Area to Cutting Edge Surface Area | | 8.1:1 | |
| Ratio-Cutting Edge Surface to P | | 0.01:1 | |
| Ratio-Interior Channel Diameter to Cutting Edge Height | | 6.1:1 | |
| Ratio-Outer Surface to Periphery Diameter | | 0.8:1 | |

Figure 14A:
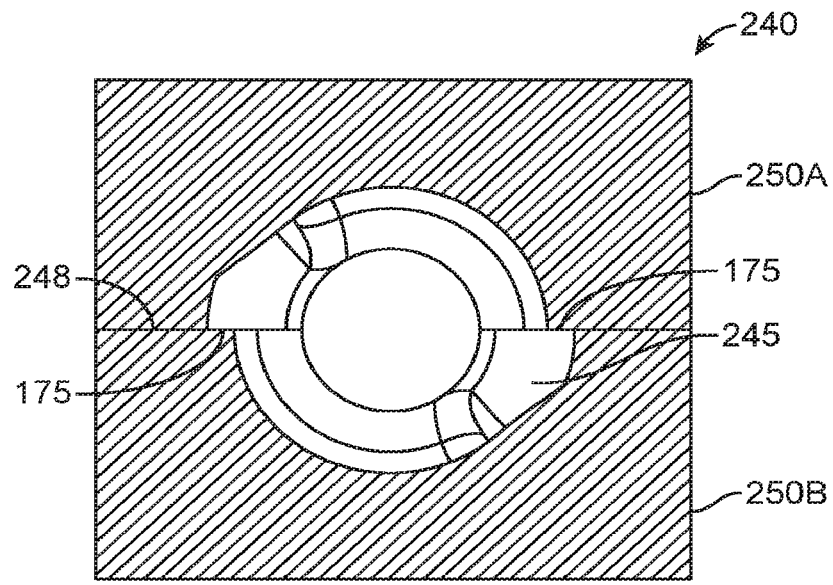
FIG. 14A is a cut-away sectional schematic view of a single-cavity ceramic injection mold illustrating a method of fabricating a ceramic cutting member with two cutting edges wherein the mold has only two parting components with a parting line on the centerline of the cutting member.
Figure 14B:
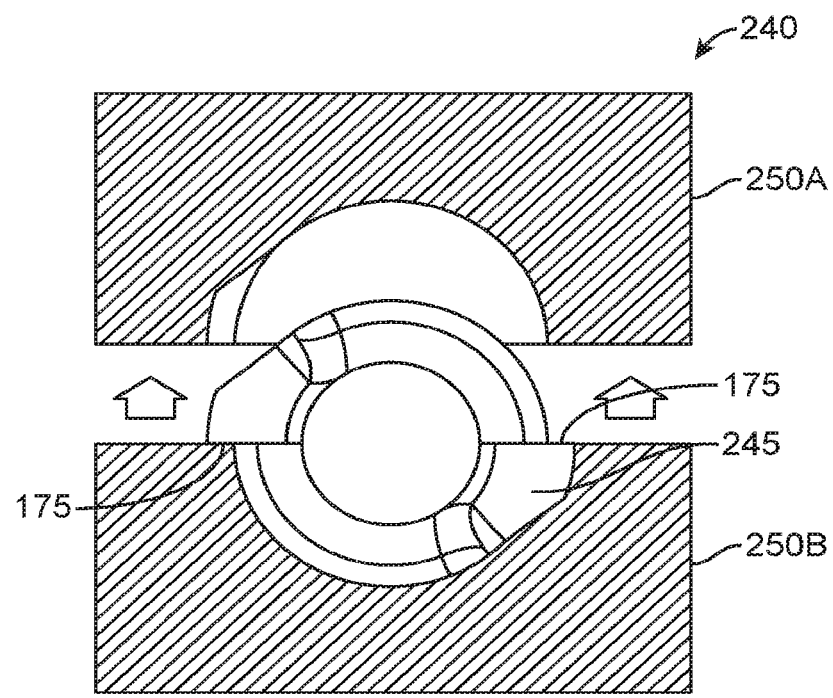
FIG. 14B another cut-away view of the injection mold of FIG. 14A showing schematically a first mold component being moved away from the green cutting member.

As described above with reference to FIGS. 8A-8B, the three component ceramic injection mold 200 with multiple cavities can be used to fabricate the green ceramic cutting members 125 which then after being released from the mold can be sintered to provide the final product. In other variations of a ceramic injection mold, FIGS. 14A-15C show two component injection molds that can be used to mold the ceramic cutting member that can have from 2 to 4 non-helical cutting edges. FIGS. 14A-14B first illustrate a two component mold 240 that is configured to mold the ceramic cutting member 245 that has two cutting edges 175. The cutting member 245 of FIG. 14A is very similar to the cutting member 125 of FIGS. 7A-7C above except for the number of cutting edges. As can be seen in FIG. 14A, the mold parting line 248 is on the centerline of the cutting member 245 so that each half of the mold (250A and 250B) can from both the shaft portion and distal cutting portion of the cutting member (cf. FIGS. 7A-7C). In this variation, there are no undercuts in the mold 240 so that a simple parting mold is possible. The core pins for the window and interior channel can be identical to those shown in FIGS. 7A-7C. An ejector pin for ejecting the green cutting member 245 from the mold 240 can be provided, but is not shown for convenience.

Figure 15A:
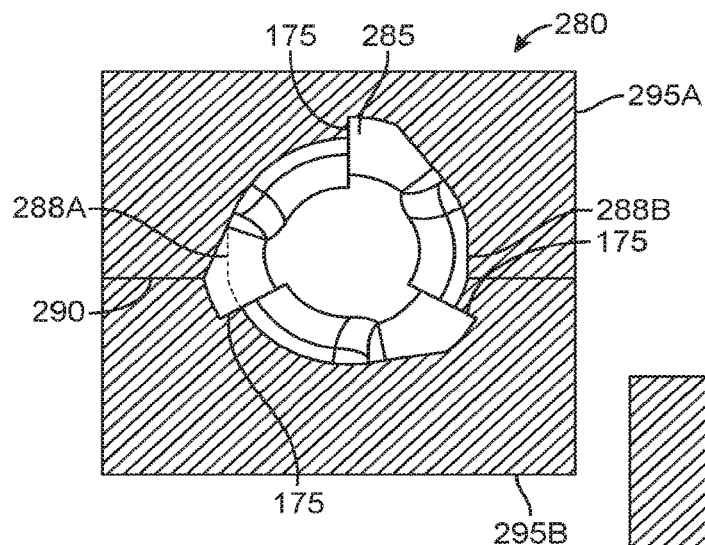
FIG. 15A is a cut-away sectional schematic view of another ceramic injection mold with only two parting components that is configured for fabricating a ceramic cutting member with three cutting edges wherein the mold has a parting line that is off-center relative to the cutting member axis.
Figure 15B:
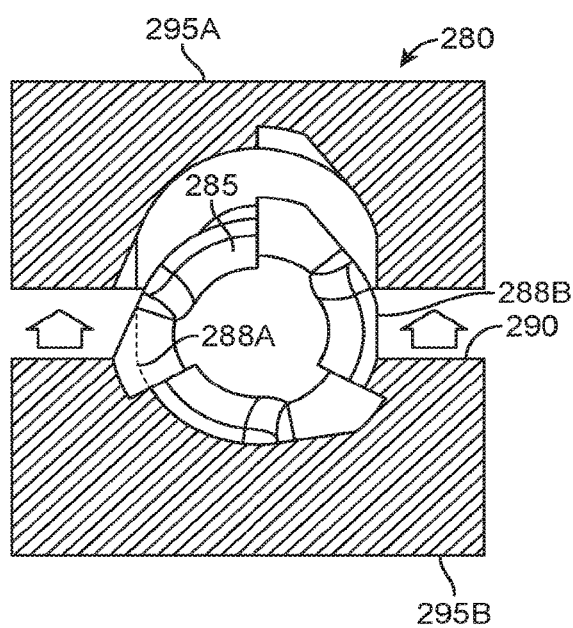
FIG. 15B another cut-away view of the injection mold of FIG. 15A showing schematically a first mold component being moved away from the cutting member axis which is enabled by flat side portions of the cutting member which eliminates undercuts.
Figure 15C:
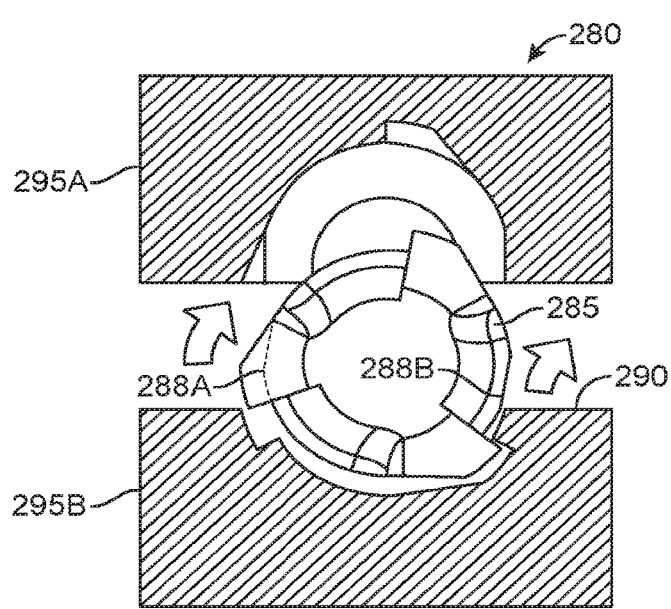
FIG. 15C another view of the injection mold of FIGS. 15A-15B showing the green cutting member being released from the mold component.

FIGS. 15A-15C show another two component injection mold 280 that can be used to mold a ceramic cutting member 285 with 3 cutting edges 175 that is virtually identical to the 3-edge cutting member 125 of FIGS. 3, 4A and 7A-7C above. This variation thus illustrates that a 3-edge cutting member 285 can be made with a simple two component (one parting line) mold rather than the more complex three component (two parting lines) mold of FIGS. 7A-7B. As can be seen in FIG. 15A, it is necessary to configure the cutting member 285 with flat surfaces 288a and 288b so that there are no undercuts in the mold 280. The parting line 290 is then can off-center. In FIGS. 15A-15B, it can be understood that the sides of the shaft portion with such flat surfaces 288a and 288b allow an upper mold component 295A to be released vertically as shown in FIG. 15B which would not be possible if the outer surface OS was not configured with the flat surfaces 288a and 288b. As shown in FIG. 15C, this variation of mold 280 allows the cutting member 285 having cutting edges 175 with zero radial rake angle to be released from the lower mold component 295B with a vertical and slight rotational movement indicated by the arrows. An ejector pin (not shown) for ejecting the green cutting member from the mold can be provided at an appropriate angle relative to the parting line 290 to push the green cutting member from the mold. This mold embodiment 280 can have core pins CP1 and CP2 as described in FIGS. 7A-7C to form the window 145 and the interior channel 126. It can be further understood from FIGS. 14A-15B that a two component parting mold with a parting line on the center of the cutting member can be used to mold a four-edge cutting member.

Figure 16A:
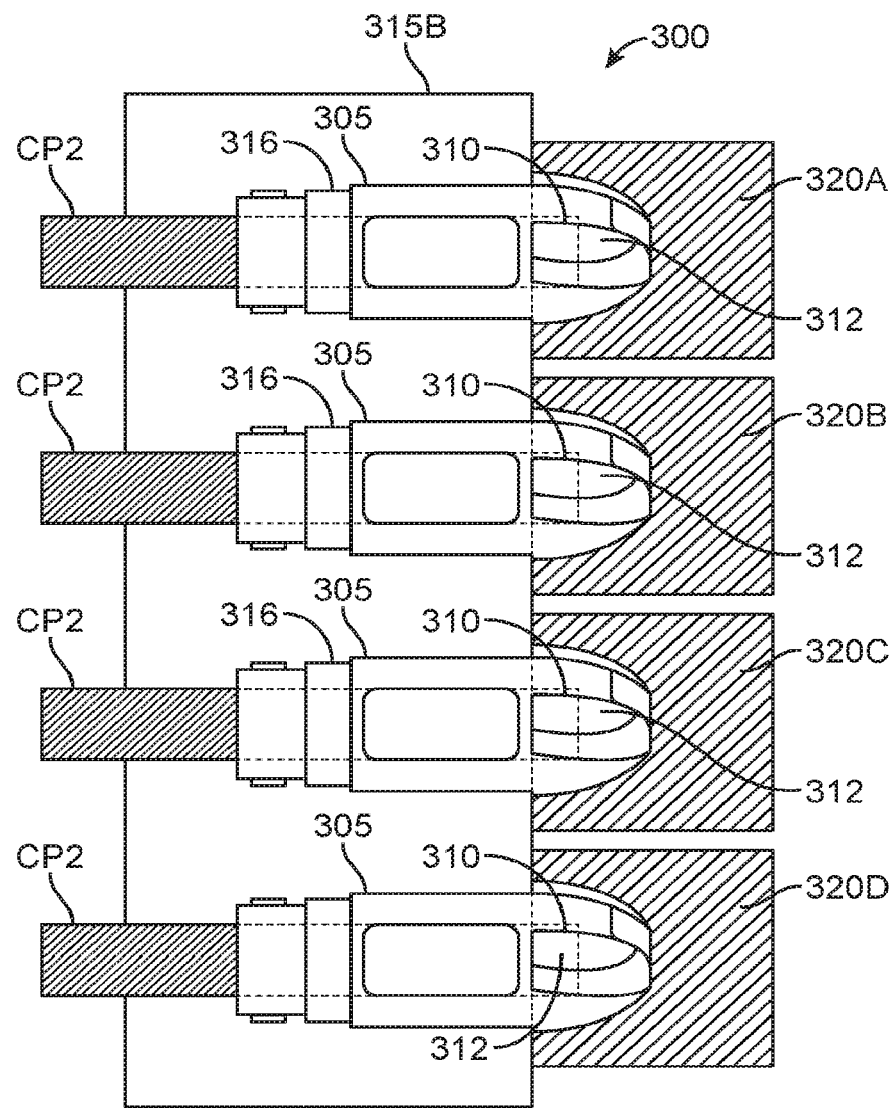
FIG. 16A is a cut-away view of another multi-cavity injection mold with some feature similar to that of FIGS. 8A-8B except that the ceramic cutting member has helical cutting edges.
Figure 16B:
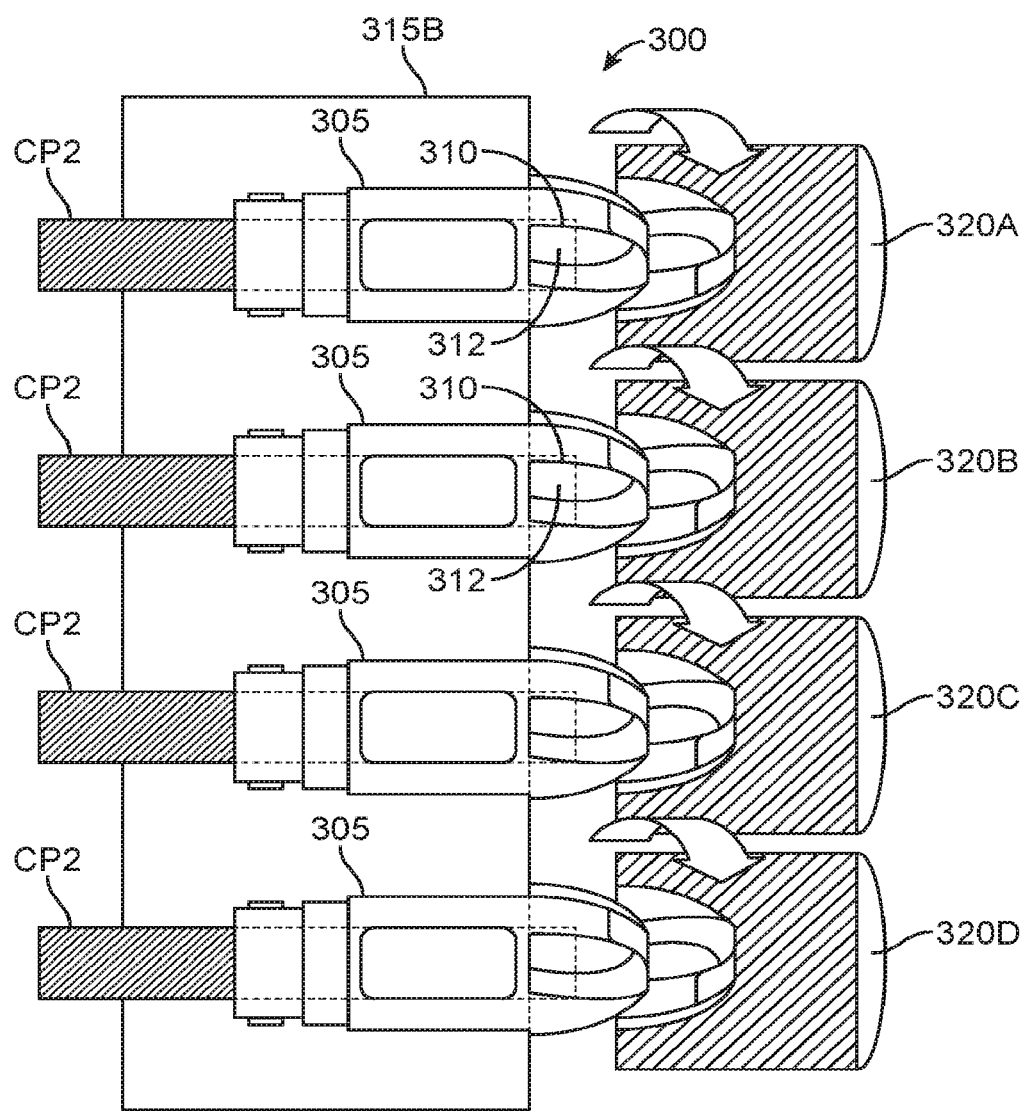
FIG. 16B shows schematically the method of helically moving mold components to release the green ceramic cutting member from its helical cutting edges.

As described above, several variations of ceramic cutter 125 have non-helical cutting edges. The non-helical edges allow for simplified ceramic injection molding. In another variation, a different type of injection mold 300 shown in FIGS. 16A-16B can be fabricated to allow for molding a cutting member 305 with helical cutting edges 310 and helical flutes 312. FIG. 16A shows an injection mold 300 with three components that is similar to that of FIGS. 8A-8B. In this embodiment, the first and second mold components 315A and 315B are adapted to part as described previously around shaft portion 316 of the cutting members 305. The third mold components indicated at 320A-320D are adapted to release from the green ceramic cutting members 305 by moving axially and rotationally (see FIG. 16B). In other words, the mold components 320A-320D are moved helically or effectively unscrewed from the cutting members 305. This mold 300 has core pins CP1 and CP2 as described previously to form the window 145 and the interior channel 126 in the cutting members.

In general a method of the invention for fabricating a surgical cutting member of a ceramic material, comprises (i) providing an injection mold with a mold cavity defining outer surfaces of a cutting member having a longitudinal axis, a distal cutting portion with cutting edges, a proximal shaft portion with a window that opens to an interior channel in the ceramic member, (ii) injecting a flowable material comprising a ceramic into the mold cavity to provide a molded ceramic member, (iii) removing a first core pin which is configured to form the window, (iv) removing a second core pin which is configured to form the interior channel and (v) parting at least first and second mold components that define the outer surfaces of the cutting member to there by release the green cutting member from the mold. The method of fabrication further comprises sintering the released cutting member to provide a hardened cutting member.

In the method of fabrication described above, the first core pin is removed in a direction orthogonal to said longitudinal axis to form the window and the second core pin is removed in a direction aligned with said longitudinal axis to form the interior channel. Of particular interest, the core pin that forms the window is configured to provides window edges that have a sharp apex 225 and have a high positive window radial rake angle WRA, for example greater than 15°. Typically, the window radial rake angle in the range of 15° to 45°, and extends from the outer surface OS to the open diameter C of the interior channel 128, which dimension in one variation can be determined from Chart B above.

In the method of fabrication described above, one mold component is moved in a direction relative to the ceramic cutter body that is orthogonal to said longitudinal axis to release the ceramic cutter body. In a variation, another mold component may be moved in a direction relative to the ceramic cutter body that is aligned with said longitudinal axis thereof to release the cutting member body. In another variation, a mold component may be moved in a direction relative to the cutting member body that is helical to release the cutting member.

A further method of fabricating the cutting member includes the mold cavity forming a proximal shaft portion having a diameter ranging between 0.150 inch and 0.50 inch. Another method of fabrication includes the mold cavity forming a distal cutting portion having an outer diameter ranging between 0.10 inch and 0.60 inch. Another method of fabrication includes the mold cavity forming non-helical cutting edges. Another method of fabrication includes the mold cavity forming cutting edges aligned with the longitudinal axis of the cutting member. Another method of fabrication includes the mold cavity forming cutting edges with a radial rake angle ranging between 0° and 5°. Another method of fabrication includes the mold cavity forming cutting edges having a length ranging 0.10 inch to 0.40 inch. Another method of fabrication includes a core pin forming the window with an area ranging from 0.01 sq. in. to 0.10 sq. in. Another method of fabrication includes a core pin forming the interior channel with a mean cross-sectional width ranging from 0.008 inch to 0.40 inch.

Figure 17:
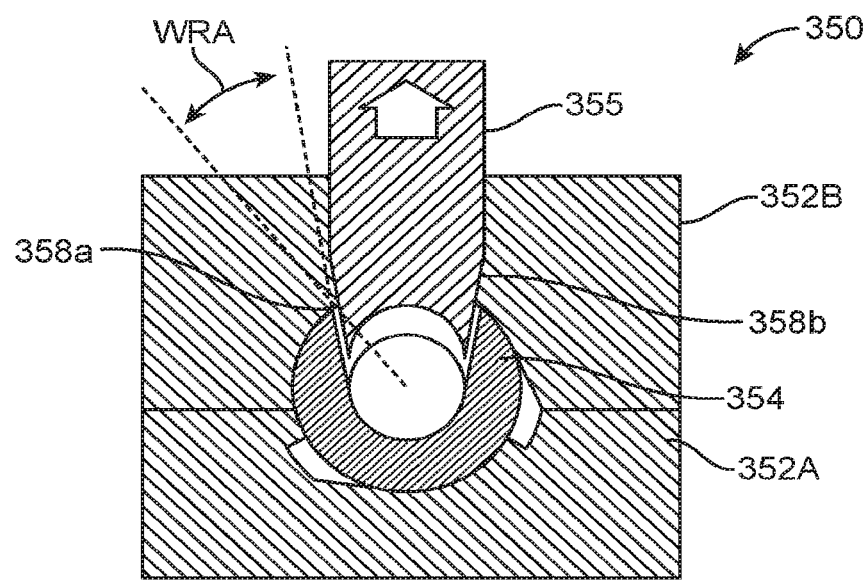
FIG. 17 is a cross-sectional view of another mold similar to those described above showing a core pin with non-parallel sides that can be used to form window edges that various positive radial rake angles.

FIG. 17 is a schematic cross-sectional view of another mold 350 with two parting components 352A and 352B to form cutting member 354 and further showing a core pin 355 partially removed from the upper mold component 352B. The core pin 355 is configured with non-parallel side portions 358A and 358b that can be used to form window edges with a range of positive window radial rake angles WRA depending on the angle of the side portions 358a and 358b.

Figure 18:
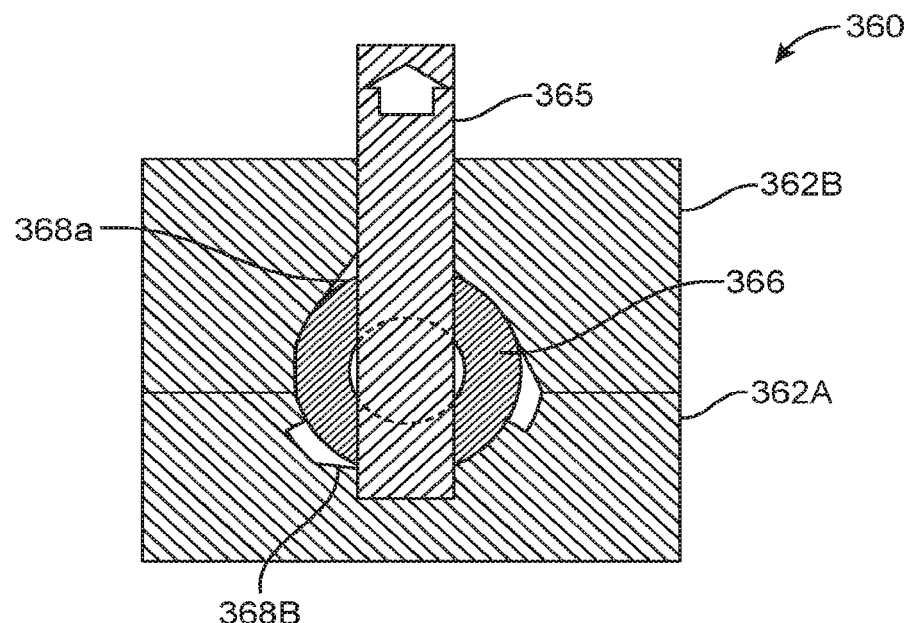
FIG. 18 is a cross-sectional view of another mold similar to those described above showing a core pin that extends through the ceramic cutting member to provide windows in both sides of the cutting member.

FIG. 18 is a schematic view of another mold 360 with two parting components 362A and 362B that shows a core pin 365 that extends through the ceramic cutting member 366 to provide windows 368A and 368B in both sides of the cutting member.

Figure 19:
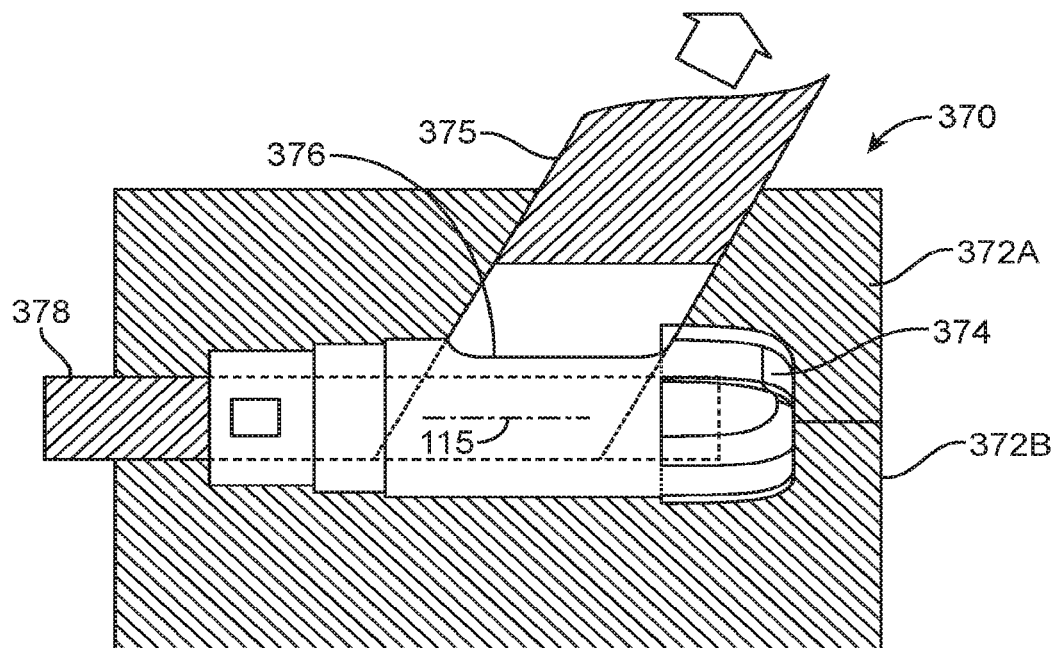
FIG. 19 is a longitudinal sectional view of another mold similar to those described above showing a core pin that for forming a window that is angled longitudinally relative to the axis of the cutting member.

FIG. 19 is a longitudinal sectional view of another mold 370 with two parting components 372A and 372B configured to form cutting member 374. In this a core pin is provided for forming a window 376 that is angled longitudinally relative to the axis 115 of the cutting member. Core pin 378 is configured for forming the interior channel in the cutting member.

Figure 20:
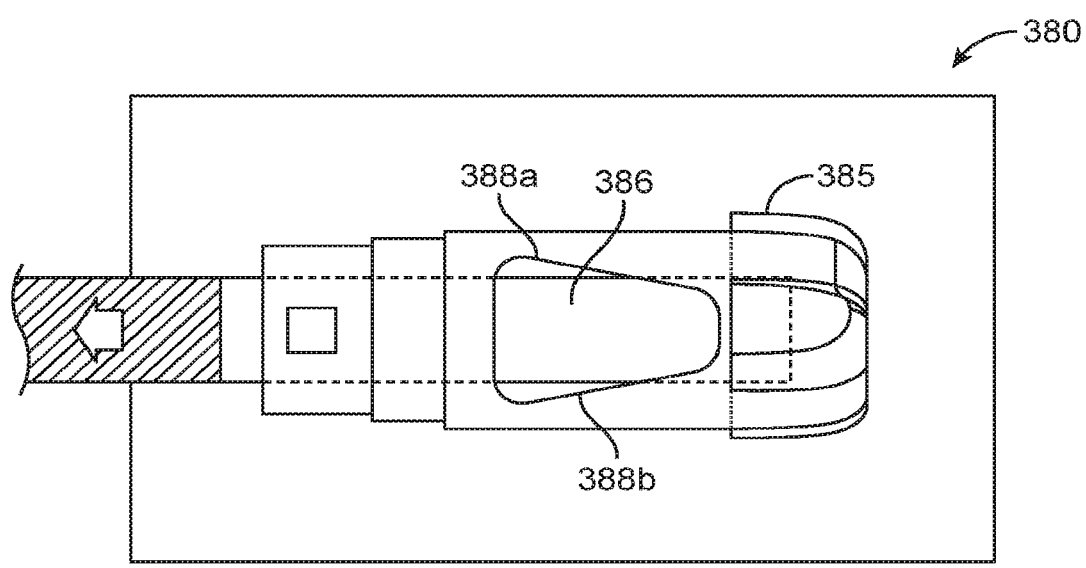
FIG. 20 is a schematic view of another mold similar to those described above showing a ceramic cutting member with a window having non-parallel sides which can be formed by a core pin.

FIG. 20 is a schematic top view of another mold 380 similar to those described above showing a ceramic cutting member 385 with a window 386 having non-parallel sides 388a and 388b which can be formed by a similarly shaped core pin. In this variation, the angled cutting edges 388a and 388b provide the advantage of shearing soft tissue captured in the window in a scissor-like manner as the angled window edges 388a and 338b progressively sweep past the lateral edges of the cut-out 144 in the outer sleeve 122 (see FIG. 1).

Figure 21:
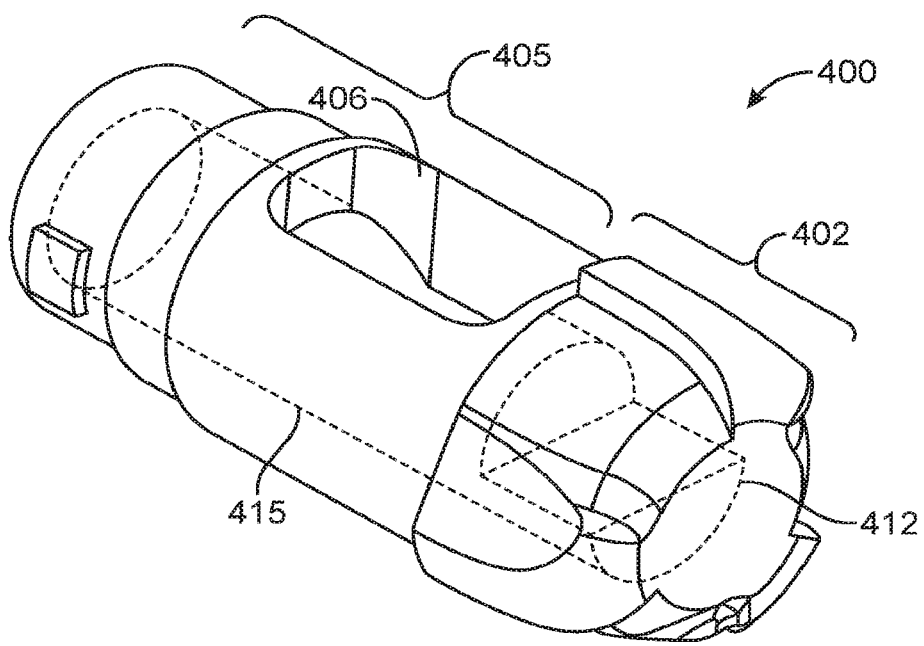
FIG. 21 is a perspective view of a cutting member similar to that of FIGS. 3 and 4A showing an interior channel that includes an off-center distal portion to create a weight asymmetry in the distal portion of the cutting member to counter-balance the weight asymmetry in the shaft portion caused by the window.
Figure 22:
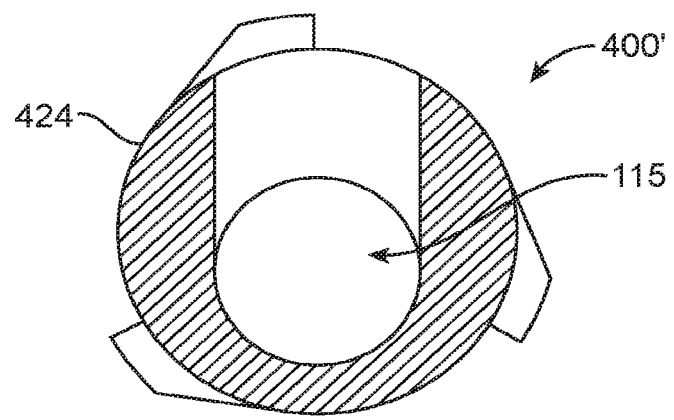
FIG. 22 is a sectional view of another cutting member similar to that of FIGS. 3 and 4A showing an off-center interior channel to create a weight asymmetry in the cutting member to counter-balance the weight asymmetry in the shaft portion caused by the window.

FIGS. 21 and 22 show another variation of ceramic cutting member 400 that is intentionally designed with rotational weight asymmetry in the distal cutting portion 402 thereof. As can be understood from FIG. 21, the proximal shaft portion 405 of the cutter is asymmetric in cross-section due to the window 406 and thus does not have a rotational weight symmetry. At high-speed rotation, for example 16,500 RPM or more, the weight asymmetry may cause a slight vibration or wobbling sensation in the handle by the operator's hand. To overcome the weight asymmetry in the proximal shaft portion 405, the variation of FIG. 21 is configured with counter-balancing weight asymmetry in the distal cutting portion 402. In one variation, the core pin CP1 as shown in FIG. 8A can be used to provide an off-center void 412 in the interior channel 415 within the distal cutting portion 402 as can be seen in FIG. 21. In another variation of cutting member 400' shown in FIG. 22, the interior channel 422 can be off center through the proximal shaft portion 424 and the distal cutting portion to balance the cutting member 400' relative to the central axis 115 of the overall cutting member.

Alternatively, another variation (not shown) can have a concavity or in the exterior surface, such as deeper flutes, in the ceramic body to provide the weight asymmetry in distal cutting portion to counter-balance the weight asymmetry in the proximal shaft portion caused by the window. In another variation (not shown), the cutting edges can be formed in various asymmetric radial positions to provide the desired weight asymmetry or the cutting edges thicknesses can vary to provide the desired weight asymmetry. In another variation, more than one of the features described above may be used to achieve the targeted weight asymmetry.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of forming a molded ceramic body for cutting tissue, the method comprising:
   injecting a flowable material comprising a ceramic material into a cavity in a mold to form a molded ceramic body that includes a longitudinal axis, a proximal shaft portion, and a distal cutting portion with a plurality of cutting edges, wherein the mold, during said injecting, accommodates a first removable core pin and a second removable core pin that extend into the cavity through a first portion of the mold and a second portion of the mold, respectively;
   removing the first removable core pin from the cavity following said injecting so as to leave a first void in the molded ceramic body, the first void forming a side window in the molded ceramic body;
   removing the second removable core pin from the cavity following said injecting so as to leave a second void in the molded ceramic body, the second void forming an interior channel that extends along the longitudinal axis in the molded ceramic body proximally and distally of the side window;
   wherein, during said injecting, the first removable core pin and the second removable core pin engage one another in the cavity so that, upon removal of the first removable core pin and the second removable core pin from the cavity following formation of the molded ceramic body, the first void and the second void are fluidly connected to one another to allow cut tissue to be drawn into the interior channel through the side window during use of the molded ceramic body; and
   removing the molded ceramic body from the cavity.

2. The method of claim 1, wherein the side window is formed in the proximal shaft portion of the molded ceramic body.

3. The method of claim 1, wherein the interior channel extends into the distal cutting portion.

4. The method of claim 1, wherein the cutting edges have a radial rake angle ranging between 0° and 5°.

5. The method of claim 1, wherein the side window includes edges with a positive radial rake angle.

6. A method of forming a molded ceramic body for cutting tissue, the method comprising:
   injecting a flowable material comprising a ceramic material into a cavity in a mold to form a molded ceramic body that includes a longitudinal axis, a proximal shaft portion, and a distal cutting portion with a plurality of cutting edges, the mold comprising a first mold component and a second mold component that are brought together to form at least part of the cavity and which are separable from one another following said injecting, wherein the mold, during said injecting, accommodates a first removable core pin and a second removable core pin that extend into the cavity through a first portion of the mold and a second portion of the mold, respectively;
   removing the first removable core pin from the cavity following said injecting so as to leave a first void in the molded ceramic body, the first void forming a side window in the molded ceramic body;
   removing the second removable core pin from the cavity following said injecting so as to leave a second void in the molded ceramic body, the second void forming an interior channel that extends along the longitudinal axis in the molded ceramic body;
   wherein, during said injecting, the first removable core pin and the second removable core pin engage one another in the cavity so that, upon removal of the first removable core pin and the second removable core pin from the cavity following formation of the molded ceramic body, the first void and the second void are fluidly connected to one another to allow cut tissue to be drawn into the interior channel through the side window during use of the molded ceramic body;
   separating the first mold component from the second component; and
   removing the molded ceramic body from the cavity.

7. The method of claim 6, wherein the side window is formed in the proximal shaft portion of the molded ceramic body.

8. The method of claim 6, wherein the molded ceramic body, once formed, is attachable to a distal end of an inner sleeve of an elongated shaft assembly, the elongated shaft assembly further including an outer sleeve in which the inner sleeve s rotatably received, wherein the interior channel in the molded ceramic body is in fluid communication with a lumen in the inner sleeve when the molded ceramic body is attached to the distal end of the inner sleeve.

9. The method of claim 6, wherein the cutting edges are helical.

10. The method of claim 6, wherein the first removable core pin is removed in a direction orthogonal to the longitudinal axis of the molded ceramic body.

11. The method of claim 6, wherein the first removable core pin is removed in a direction angled to the longitudinal axis of the molded ceramic body.

12. The method of claim 6, wherein the first mold component is separated from the second mold component in a direction orthogonal to the longitudinal axis of the molded ceramic body.

13. The method of claim 6, wherein the first mold component is separated from the second mold component in a direction aligned with the longitudinal axis of the molded ceramic body.

14. The method of claim 6, wherein the first mold component and the second mold component form the distal cutting portion of the molded ceramic body.

15. The method of claim 6, wherein the cutting edges are non-helical.

16. The method of claim 15, wherein the cutting edges are aligned with the longitudinal axis of the molded ceramic body.

17. The method of claim 6, wherein the mold further comprises a third mold component that forms at least part of the cavity.

18. The method of claim 17, wherein the third mold component forms the distal cutting portion of the molded ceramic body.

19. A method of forming a molded ceramic body for cutting tissue, the method comprising:
    injecting a flowable material comprising a ceramic material into a cavity in a mold to form a molded ceramic body that includes a longitudinal axis, a proximal shaft portion, and a distal cutting portion with a plurality of cutting edges, wherein the mold, during said injecting, accommodates a first removable core pin and a second removable core pin that extend into the cavity through a first portion of the mold and a second portion of the mold, respectively;
    removing the first removable core pin from the cavity following said injecting so as to leave a first void in the molded ceramic body, the first void forming a side window in the proximal shaft portion of the molded ceramic body;
    removing the second removable core pin from the cavity following said injecting so as to leave a second void in the molded ceramic body, the second void forming an interior channel that extends along the longitudinal axis in the molded ceramic body;
    wherein, during said injecting, the first removable core pin and the second removable core pin engage one another in the cavity so that, upon removal of the first removable core pin and the second removable core pin from the cavity following formation of the molded ceramic body, the first void and the second void are fluidly connected to one another to allow cut tissue to be drawn into the interior channel through the side window during use of the molded ceramic body; and
    removing the molded ceramic body from the cavity.

20. The method of claim 19, wherein the interior channel extends into the distal cutting portion.

* * * * *